United States Patent [19]

Schrader et al.

[11] Patent Number: 6,146,887
[45] Date of Patent: Nov. 14, 2000

[54] DNA EXPRESSION VECTORS FOR USE IN THE GENE THERAPEUTIC TREATMENT OF VASCULAR DISORDERS

[75] Inventors: Jürgen Schrader; Axel Gödecke, both of Düsseldorf, Germany

[73] Assignee: Jurgen Schrader, Dusseldorf, Germany

[21] Appl. No.: 09/123,708

[22] Filed: Jul. 28, 1998

Related U.S. Application Data

[63] Continuation of application No. 08/553,503, filed as application No. PCT/EP95/01202, Mar. 31, 1995, abandoned.

[30] Foreign Application Priority Data

Mar. 31, 1994 [DE] Germany .............................. 44 11 402

[51] Int. Cl.$^7$ ................................................... C12N 15/00
[52] U.S. Cl. .................... 435/320.1; 435/69.1; 435/440; 514/44; 514/12; 536/23.2; 536/23.5
[58] Field of Search .............................. 435/320.1, 69.1, 435/440; 514/44, 12; 536/23.2, 23.5

[56] References Cited

U.S. PATENT DOCUMENTS

| | | | |
|---|---|---|---|
| 5,132,407 | 7/1992 | Stuehr et al. | 530/395 |
| 5,252,479 | 10/1993 | Srivastava | 435/235.1 |
| 5,328,470 | 7/1994 | Nabel et al. | 604/101 |
| 5,428,070 | 6/1995 | Cooke et al. | 514/557 |
| 5,468,630 | 11/1995 | Billiar et al. | 435/189 |
| 5,658,565 | 8/1997 | Billiar et al. | 424/93.21 |
| 5,766,909 | 6/1998 | Xie et al. | 435/189 |

FOREIGN PATENT DOCUMENTS

| | | |
|---|---|---|
| 0546796 | 6/1993 | European Pat. Off. . |
| 0441119 | 8/1993 | European Pat. Off. . |
| WO92/07943 | 5/1992 | WIPO . |
| WO93/18156 | 9/1993 | WIPO . |
| WO94/12645 | 6/1994 | WIPO . |
| WO94/23038 | 10/1994 | WIPO . |
| WO94/24269 | 10/1994 | WIPO . |
| WO94/28721 | 12/1994 | WIPO . |
| WO95/27070 | 10/1995 | WIPO . |
| WO96/00006 | 1/1996 | WIPO . |
| WO98/02170 | 1/1998 | WIPO . |

OTHER PUBLICATIONS

Steg et al. "Local Delivery of Adenovirus for Percutaneous Arterial Gener Transfer" Abstract 3554; Circulation vol. 88, No. 4(2) Oct. 1993, p. I–660.

Werner–Felmayer et al, "Tetrahydrobiopterin–Dependent Formation of Nitrite and Nitrate in Murine Fibroblasts" 1990 J. Exp. Med.172: 1599–1607.

Nature, vol. 333, Jun. 16, 1988, pp. 664–666.

Biochem, Biophys. Res. Commun., vol. 153, No. 3, Jun. 30, 1988, pp. 1251–1256.

Gen. Pharmac, vol. 21, No. 5, 1990, pp. 575–587.

J. Clin, Invest, vol. 90, 1992, pp. 1168–1172.

J. Clin. Invest., vol. 90, 1992, pp. 1248–1253.

Biochem, Biophysc. Res. Communc., vol. 191, No. 1, Feb. 26, 1993, pp. 89–94.

Nunokawa et al., Cloning of Inducible Nitric Ozide Synthase in Rat Vascular Smooth Muscle Cells, *BioChemical and Biophysical Research Communications;* vol. 191, No. 1, Feb. 26, 1993, pp. 89–94.

Bucala, et al., "Advanced Glycosylation Products Quench Nitric Oxide and Mediate Defective Endothelium–Dependant Vasodilalation in Experimental Diabetes" 1991 J. Clin. Invest. 87: 432–438.

Charles et al.; "Cloning, Characterization and Expression of a cDNA Encoding an Induable Nitric Oxide Synthase From the Human Chondrocye" Proc. Nat'l Acad. Sci USA 1993; Dec. 1, 90(23):11419–11423 (1993), Abstract.

Charles et al.; "Cloning and Expression of a Rat Neuronal Nitric Oxide Synthase Coding Sequence in a Baculovirus/Insect Cell System" Biochemical and Biophysical Research Communications, vol. 196, No. 3, 1481–1489 (1993).

Chester et al., "Low Basal and stimulated Release of Nitric Oxide in Atherosclerotic Epicardial Coronary Arteries" 1990, Lancet 336: 897–900.

Chin et al., "Inactivation of Endothelial Derived Relaxing Factory by Oxidized Lipoproteins" 1992, J. Clin. Invest. 89:10–18.

Clowes et al. "Kinetics of Cellular Proliferation After Arterial Injury" (1983) 327–333.

Draiper et al., "L–arginine–derived Nitric Oxide and the Cell–Mediated Immune Response" 1991 Res. Immunol. 142:553–602.

Förstermann et al. v Eurpoean Heart Journal (1993) 14 (Supp. I), "Isoforms of Nitric Oxide Synthase: Functions in the Cardiovascular System".

Feldman et al. "Site Specificity of Adernovirus—Medicated Gene Transfer by Hydrogelated Balloon" (Abstract) JACC Feb. 1994:1A–484A (p. 235A).

Geller et al., "Molecular Cloning and Expression of Inducible Nitric Oxide Synthase from Human Hepatocytes" 1993 PNAS 90: 3491–3495.

Geller et al.; "Should Surgeons Clone Genes" Archives of Surgery; American Medical Association vol. 128 p. 1212–1220 (Nov. 1993).

Ignarro et al. "Endothelium–Derived Relaxing Factor Produced and Released from Artery and Vein in Nitric Oxide" 1987 PNAS 84: 9265–9269.

Janssens et al.; "Cloning and Expression of a cDNA Encoding Human Endothelium–Derived Relaxing Factor/Nitric Oxide Synthase" The Journal of Biological Chemistry; vol. 267, No. 21 Issue of Jul. 25 pp. 14319–14522 (1992).

(List continued on next page.)

*Primary Examiner*—Jezia Riley
*Attorney, Agent, or Firm*—Frommer Lawrence & Haug

[57] ABSTRACT

A DNA expression vector is described which is characterized in that it comprises a DNA sequence that codes a protein which possesses the biological activity of nitrogen monoxide synthase (NOS) and eukaryotic regulation elements, wherein said eukaryotic regulation elements result in the expression of said DNA sequence in eukaryotic cells, as well as the use of the expression vector for treatment or prevention of vascular disorders.

9 Claims, 24 Drawing Sheets

OTHER PUBLICATIONS

Lange et al. Southwestern Internal Medicine Conference:Restenosis (Od. 1983) p. 265–275.

Lloyd–Jones, M.D. et al.; "The Vascular Biology of Nitric Oxide and its Role In Atherogenesis" Annu. Rev. Med. 1996, 47:365–75.

Lowenstein et al.; "Cloned and expressed macrophage nitric oxide synthase contrasts with the brain enzyme" Proc. Nat'l Acad. Sci. USA; vol. 89, pp. 6711–6715, Aug. 1992.

Lyons et al., "Molecular Cloning and Functional Expression of an Inducible Nitric Oxide Synthase from a Murine Macrophage Cell Line" 1992 J. Biol. Chem. 267:6370–6374.

Moncada, et al. 1991, "Nitric Oxide: Physiology, Pathophysiology and Pharmacology Pharmaceuticals Reviews 43: 109–142.

Nabel et al. "Recombinant Gene Expression In Vivo within Endothelial Cells of the Arterial Wall" *Science* 244: 1342–1344 (1989).

Nabel et al. "Site–specific Gene Expression In Vivo by Direct Gene Transfer into the Arterial Wall" 1990, Science 249:1285–1288.

Nakane et al.; "Cloned Human Brain Nitric Oxide Synthase is Highly Expressed in Skeletal Muscle" FEBS Letters, vol. 316, No. 2, 175–180; Jan. 1993.

Nakanishi et al. Efficient Intorduction of Contents of Liposomes into Cells Using Hr3 (Sendai Virus) (1985) 399–409.

Nunokawa and Tanaka, "Interferon–Gamma Inhibits Proliferation of Rat Vascular Smooth Muscle Cells by Nitric Oxide Generation" 1992, Biochem Biophys. Res. Comm. 188: 409–415.

Nussler et al. "Stimulation of Nitric Oxide in Human Hepatocytes by Cytokines" 1992 Faseb. J., 6(5):A1834(#5200).

Nussler, et al. "Stimulation of the Nitric Oxide Synthase Pathway in Human Hepatocytes by Cytokines and Endotoxins" 1992, J. Exp. Med. 176: 261–264.

Radomski et al., "The Anti–Aggregating Properties of Vascular Endothelium: Interactions Between Prostacyclin and Nitric Oxide" 1987 Br. J. Pharmac. 92:639–646.

Sessa; "Molecular Cloning and Expression of a cDNA Encoding Endothelial Cell Nitric Oxide Synthase" The Journal of Biological Chemistry; vol. 267, No. 22, Issue of Aug. 5, pp. 15274–15276, 1992.

Steg et al. Local Delivery of Adenovirus for Percutaneous Arterial Gene Transfer (abstract) Supplement to Circulation, vol. 88, No. 4, Para 2 (Oct. 1993).

von der Leyen et al., "In Vivo Gene Transfer to Prevent Neointima Hyperplasia after Vascular Injury: Effect of Overexpression of Constitutive Nitric Oxide Synthase" 1994 Faseb. J. 8:A802 (#4651).

von der Leyen et al., "Gene Therapy Inhibiting Vascular Lesion: In Vivo Transfer of Endothelial Cell Nitric Oxide Synthase Gene" pNAS USA 92 pp. 1137–1141 (Feb. 1995).

Wilson et al., "Implantation of Vascular Grafts Lines with Genetically Modified Endothelial Cells" 1989, Science 244:1344–1346.

Xie, et al. "Cloning and Characterization of Inducible Nitric Oxide Synthase from Mouse Macrophages" 1992 Science 256:225–228.

Zwiebel et al. "High–Level Recombinant Gene Expression in Rabbit Endothelial Cells Transduced by Retroviral Vectors" 1989, Science 243: 220–222.

Fig. 1

```
GAGACTCTGG CCCCACGGGA CACAGTGTCA CTGGTTTGAA ACTTCTCAGC CACCTTGGTG      60

AAGGGACTGA GCTGTTAGAG ACACTTCTGA GGCTCCTCAC GCTTGGGTCT TGTTCACTCC     120

ACGGAGTAGC CTAGTCAACT GCAAGAGAAC GGAGAACGTT GGATTTGGAG CAGAAGTGCA     180

AAGTCTCAGA C ATG GCT TGC CCC TGG AAG TTT CTC TTC AAA GTC AAA TCC      230
            Met Ala Cys Pro Trp Lys Phe Leu Phe Lys Val Lys Ser
             1           5                        10
```

| | | | | | | | | | | | | | | | |
|---|---|---|---|---|---|---|---|---|---|---|---|---|---|---|---|
| TAC | CAA | AGT | GAC | CTG | AAA | GAG | GAA | AAG | GAC | ATT | AAC | AAC | AAC | GTG | AAG | 278
| Tyr | Gln | Ser | Asp | Leu | Lys | Glu | Glu | Lys | Asp | Ile | Asn | Asn | Asn | Val | Lys |
| | 15 | | | | 20 | | | | | 25 | | | | | |

```
AAA ACC CCT TGT GCT GTT CTC AGC CCA ACA ATA CAA GAT GAC CCT AAG      326
Lys Thr Pro Cys Ala Val Leu Ser Pro Thr Ile Gln Asp Asp Pro Lys
 30              35                  40                      45

AGT CAC CAA AAT GGC TCC CCG CAG CTC CTC ACT GGG ACA GCA CAG AAT      374
Ser His Gln Asn Gly Ser Pro Gln Leu Leu Thr Gly Thr Ala Gln Asn
                50                  55                  60

GTT CCA GAA TCC CTG GAC AAG CTG CAT GTG ACA TCG ACC CGT CCA CAG      422
Val Pro Glu Ser Leu Asp Lys Leu His Val Thr Ser Thr Arg Pro Gln
             65                  70                  75

TAT GTG AGG ATC AAA AAC TGG GGC AGT GGA GAG ATT TTG CAT GAC ACT      470
Tyr Val Arg Ile Lys Asn Trp Gly Ser Gly Glu Ile Leu His Asp Thr
             80                  85                  90

CTT CAC CAC AAG GCC ACA TCG GAT TTC ACT TGC AAG TCC AAG TCT TGC      518
Leu His His Lys Ala Thr Ser Asp Phe Thr Cys Lys Ser Lys Ser Cys
         95              100                 105

TTG GGG TCC ATC ATG AAC CCC AAG AGT TTG ACC AGA GGA CCC AGA GAC      566
Leu Gly Ser Ile Met Asn Pro Lys Ser Leu Thr Arg Gly Pro Arg Asp
110                 115                 120                 125

AAG CCT ACC CCT CTG GAG GAG CTC CTG CCT CAT GCC ATT GAG TTC ATC      614
Lys Pro Thr Pro Leu Glu Glu Leu Leu Pro His Ala Ile Glu Phe Ile
                130                 135                 140

AAC CAG TAT TAT GGC TCC TTT AAA GAG GCA AAA ATA GAG GAA CAT CTG      662
Asn Gln Tyr Tyr Gly Ser Phe Lys Glu Ala Lys Ile Glu Glu His Leu
            145                 150                 155

GCC AGG CTG GAA GCT GTA ACA AAG GAA ATA GAA ACA ACA GGA ACC TAC      710
Ala Arg Leu Glu Ala Val Thr Lys Glu Ile Glu Thr Thr Gly Thr Tyr
        160                 165                 170

CAG CTC ACT CTG GAT GAG CTC ATC TTT GCC ACC AAG ATG GCC TGG AGG      758
Gln Leu Thr Leu Asp Glu Leu Ile Phe Ala Thr Lys Met Ala Trp Arg
    175                 180                 185

AAT GCC CCT CGC TGC ATC GGC AGG ATC CAG TGG TCC AAC CTG CAG GTC      806
Asn Ala Pro Arg Cys Ile Gly Arg Ile Gln Trp Ser Asn Leu Gln Val
190             195                 200                 205
```

Fig. 1 continuation

```
TTT GAC GCT CGG AAC TGT AGC ACA GCA CAG GAA ATG TTT CAG CAC ATC        854
Phe Asp Ala Arg Asn Cys Ser Thr Ala Gln Glu Met Phe Gln His Ile
                210                 215                 220

TGC AGA CAC ATA CTT TAT GCC ACC AAC AAT GGC AAC ATC AGG TCG GCC        902
Cys Arg His Ile Leu Tyr Ala Thr Asn Asn Gly Asn Ile Arg Ser Ala
                225                 230                 235

ATC ACT GTG TTC CCC CAG CGG AGT GAC GGC AAA CAT GAC TTC AGG CTC        950
Ile Thr Val Phe Pro Gln Arg Ser Asp Gly Lys His Asp Phe Arg Leu
                240                 245                 250

TGG AAT TCA CAG CTC ATC CGG TAC GCT GGC TAC CAG ATG CCC GAT GGC        998
Trp Asn Ser Gln Leu Ile Arg Tyr Ala Gly Tyr Gln Met Pro Asp Gly
        255                 260                 265

ACC ATC AGA GGG GAT GCT GCC ACC TTG GAG TTC ACC CAG TTG TGC ATC        1046
Thr Ile Arg Gly Asp Ala Ala Thr Leu Glu Phe Thr Gln Leu Cys Ile
270                 275                 280                 285

GAC CTA GGC TGG AAG CCC CGC TAT GGC CGC TTT GAT GTG CTG CCT CTG        1094
Asp Leu Gly Trp Lys Pro Arg Tyr Gly Arg Phe Asp Val Leu Pro Leu
                290                 295                 300

GTC TTG CAA GCT GAT GGT CAA GAT CCA GAG GTC TTT GAA ATC CCT CCT        1142
Val Leu Gln Ala Asp Gly Gln Asp Pro Glu Val Phe Glu Ile Pro Pro
                305                 310                 315

GAT CTT GTG TTG GAG GTG ACC ATG GAG CAT CCC AAG TAC GAG TGG TTC        1190
Asp Leu Val Leu Glu Val Thr Met Glu His Pro Lys Tyr Glu Trp Phe
                320                 325                 330

CAG GAG CTC GGG TTG AAG TGG TAT GCA CTG CCT GCC GTG GCC AAC ATG        1238
Gln Glu Leu Gly Leu Lys Trp Tyr Ala Leu Pro Ala Val Ala Asn Met
        335                 340                 345

CTA CTG GAG GTG GGT GGC CTC GAA TTC CCA GCC TGC CCC TTC AAT GGT        1286
Leu Leu Glu Val Gly Gly Leu Glu Phe Pro Ala Cys Pro Phe Asn Gly
350                 355                 360                 365

TGG TAC ATG GGC ACC GAG ATT GGA GTT CGA GAC TTC TGT GAC ACA CAG        1334
Trp Tyr Met Gly Thr Glu Ile Gly Val Arg Asp Phe Cys Asp Thr Gln
                370                 375                 380

CGC TAC AAC ATC CTG GAG GAA GTG GGC CGA AGG ATG GGC CTG GAG ACC        1382
Arg Tyr Asn Ile Leu Glu Glu Val Gly Arg Arg Met Gly Leu Glu Thr
                385                 390                 395

CAC ACA CTG GCC TCC CTC TGG AAA GAC CGG GCT GTC ACG GAG ATC AAT        1430
His Thr Leu Ala Ser Leu Trp Lys Asp Arg Ala Val Thr Glu Ile Asn
            400                 405                 410

GTG GCT GTG CTC CAT AGT TTC CAG AAG CAG AAT GTG ACC ATC ATG GAC        1478
Val Ala Val Leu His Ser Phe Gln Lys Gln Asn Val Thr Ile Met Asp
            415                 420                 425

CAC CAC ACA GCC TCA GAG TCC TTC ATG AAG CAC ATG CAG AAT GAG TAC        1526
His His Thr Ala Ser Glu Ser Phe Met Lys His Met Gln Asn Glu Tyr
430                 435                 440                 445
```

Fig. 1 continuation

```
CGG GCC CGT GGA GGC TGC CCG GCA GAC TGG ATT TGG CTG GTC CCT CCA        1574
Arg Ala Arg Gly Gly Cys Pro Ala Asp Trp Ile Trp Leu Val Pro Pro
                450                 455                 460

GTG TCT GGG AGC ATC ACC CCT GTG TTC CAC CAG GAG ATG TTG AAC TAT        1622
Val Ser Gly Ser Ile Thr Pro Val Phe His Gln Glu Met Leu Asn Tyr
            465                 470                 475

GTC CTA TCT CCA TTC TAC TAC TAC CAG ATC GAG CCC TGG AAG ACC CAC        1670
Val Leu Ser Pro Phe Tyr Tyr Tyr Gln Ile Glu Pro Trp Lys Thr His
        480                 485                 490

ATC TGG CAG AAT GAG AAG CTG AGG CCC AGG AGG AGA GAG ATC CGA TTT        1718
Ile Trp Gln Asn Glu Lys Leu Arg Pro Arg Arg Arg Glu Ile Arg Phe
    495                 500                 505

AGA GTC TTG GTG AAA GTG GTG TTC TTT GCT TCC ATG CTA ATG CGA AAG        1766
Arg Val Leu Val Lys Val Val Phe Phe Ala Ser Met Leu Met Arg Lys
510                 515                 520                 525

GTC ATG GCT TCA CGG GTC AGA GCC ACA GTC CTC TTT GCT ACT GAG ACA        1814
Val Met Ala Ser Arg Val Arg Ala Thr Val Leu Phe Ala Thr Glu Thr
                530                 535                 540

GGG AAG TCT GAA GCA CTA GCC AGG GAC CTG GCC ACC TTG TTC AGC TAC        1862
Gly Lys Ser Glu Ala Leu Ala Arg Asp Leu Ala Thr Leu Phe Ser Tyr
            545                 550                 555

GCC TTC AAC ACC AAG GTT GTC TGC ATG GAC CAG TAT AAG GCA AGC ACC        1910
Ala Phe Asn Thr Lys Val Val Cys Met Asp Gln Tyr Lys Ala Ser Thr
        560                 565                 570

TTG GAA GAG GAG CAA CTA CTG CTG GTG GTG ACA AGC ACA TTT GGG AAT        1958
Leu Glu Glu Glu Gln Leu Leu Leu Val Val Thr Ser Thr Phe Gly Asn
    575                 580                 585

GGA GAC TGT CCC AGC AAT GGG CAG ACT CTG AAG AAA TCT CTG TTC ATG        2006
Gly Asp Cys Pro Ser Asn Gly Gln Thr Leu Lys Lys Ser Leu Phe Met
590                 595                 600                 605

CTT AGA GAA CTC AAC CAC ACC TTC AGG TAT GCT GTG TTT GGC CTT GGC        2054
Leu Arg Glu Leu Asn His Thr Phe Arg Tyr Ala Val Phe Gly Leu Gly
                610                 615                 620

TCC AGC ATG TAC CCT CAG TTC TGC GCC TTT GCT CAT GAC ATC GAC CAG        2102
Ser Ser Met Tyr Pro Gln Phe Cys Ala Phe Ala His Asp Ile Asp Gln
            625                 630                 635

AAG CTG TCC CAC CTG GGA GCC TCT CAG CTT GCC CCA ACA GGA GAA GGG        2150
Lys Leu Ser His Leu Gly Ala Ser Gln Leu Ala Pro Thr Gly Glu Gly
        640                 645                 650

GAC GAA CTC AGT GGG CAG GAG GAT GCC TTC CGC AGC TGG GCT GTA CAA        2198
Asp Glu Leu Ser Gly Gln Glu Asp Ala Phe Arg Ser Trp Ala Val Gln
    655                 660                 665

ACC TTC CGG GCA GCC TGT GAG ACC TTT GAT GTC CGA AGC AAA CAT CAC        2246
Thr Phe Arg Ala Ala Cys Glu Thr Phe Asp Val Arg Ser Lys His His
670                 675                 680                 685
```

Fig. 1 continuation

```
ATT CAG ATC CCG AAA CGC TTC ACT TCC AAT GCA ACA TGG GAG CCA CAG    2294
Ile Gln Ile Pro Lys Arg Phe Thr Ser Asn Ala Thr Trp Glu Pro Gln
            690             695                 700

CAA TAT AGG CTC ATC CAG AGC CCG GAG CCT TTA GAC CTC AAC AGA GCC    2342
Gln Tyr Arg Leu Ile Gln Ser Pro Glu Pro Leu Asp Leu Asn Arg Ala
            705             710                 715

CTC AGC AGC ATC CAT GCA AAG AAC GTG TTT ACC ATG AGG CTG AAA TCC    2390
Leu Ser Ser Ile His Ala Lys Asn Val Phe Thr Met Arg Leu Lys Ser
            720             725                 730

CAG CAG AAT CTG CAG AGT GAA AAG TCC AGC CGC ACC ACC CTC CTC GTT    2438
Gln Gln Asn Leu Gln Ser Glu Lys Ser Ser Arg Thr Thr Leu Leu Val
            735             740                 745

CAG CTC ACC TTC GAG GGC AGC CGA GGG CCC AGC TAC CTG CCT GGG GAA    2486
Gln Leu Thr Phe Glu Gly Ser Arg Gly Pro Ser Tyr Leu Pro Gly Glu
750             755             760                 765

CAC CTG GGG ATC TTC CCA GGC AAC CAG ACC GCC CTG GTG CAG GGA ATC    2534
His Leu Gly Ile Phe Pro Gly Asn Gln Thr Ala Leu Val Gln Gly Ile
                770             775                 780

TTG GAG CGA GTT GTG GAT TGT CCT ACA CCA CAC CAA ACT GTG TGC CTG    2582
Leu Glu Arg Val Val Asp Cys Pro Thr Pro His Gln Thr Val Cys Leu
            785             790                 795

GAG GTT CTG GAT GAG AGC GGC AGC TAC TGG GTC AAA GAC AAG AGG CTG    2630
Glu Val Leu Asp Glu Ser Gly Ser Tyr Trp Val Lys Asp Lys Arg Leu
            800             805                 810

CCC CCC TGC TCA CTC AGC CAA GCC CTC ACC TAC TTC CTG GAC ATT ACG    2678
Pro Pro Cys Ser Leu Ser Gln Ala Leu Thr Tyr Phe Leu Asp Ile Thr
            815             820                 825

ACC CCT CCC ACC CAG CTG CAG CTC CAC AAG CTG GCT CGC TTT GCC ACG    2726
Thr Pro Pro Thr Gln Leu Gln Leu His Lys Leu Ala Arg Phe Ala Thr
830             835             840                 845

GAC GAG ACG GAT AGG CAG AGA TTG GAG GCC TTG TGT CAG CCC TCA GAG    2774
Asp Glu Thr Asp Arg Gln Arg Leu Glu Ala Leu Cys Gln Pro Ser Glu
            850             855                 860

TAC AAT GAC TGG AAG TTC AGC AAC AAC CCC ACG TTC CTG GAG GTG CTT    2822
Tyr Asn Asp Trp Lys Phe Ser Asn Asn Pro Thr Phe Leu Glu Val Leu
            865             870                 875

GAA GAG TTC CCT TCC TTG CAT GTG CCC GCT GCC TTC CTG CTG TCG CAG    2870
Glu Glu Phe Pro Ser Leu His Val Pro Ala Ala Phe Leu Leu Ser Gln
            880             885                 890

CTC CCT ATC TTG AAG CCC CGC TAC TAC TCC ATC AGC TCC TCC CAG GAC    2918
Leu Pro Ile Leu Lys Pro Arg Tyr Tyr Ser Ile Ser Ser Ser Gln Asp
            895             900                 905

CAC ACC CCC TCG GAG GTT CAC CTC ACT GTG GCC GTG GTC ACC TAC CGC    2966
His Thr Pro Ser Glu Val His Leu Thr Val Ala Val Val Thr Tyr Arg
910             915             920                 925
```

Fig. 1 continuation

```
ACC CGA GAT GGT CAG GGT CCC CTG CAC CAT GGT GTC TGC AGC ACT TGG        3014
Thr Arg Asp Gly Gln Gly Pro Leu His His Gly Val Cys Ser Thr Trp
                930                 935                 940

ATC AGG AAC CTG AAG CCC CAG GAC CCA GTG CCC TGC TTT GTG CGA AGT        3062
Ile Arg Asn Leu Lys Pro Gln Asp Pro Val Pro Cys Phe Val Arg Ser
                945                 950                 955

GTC AGT GGC TTC CAG CTC CCT GAG GAC CCC TCC CAG CCT TGC ATC CTC        3110
Val Ser Gly Phe Gln Leu Pro Glu Asp Pro Ser Gln Pro Cys Ile Leu
            960                 965                 970

ATT GGG CCT GGT ACG GGC ATT GCT CCC TTC CGA AGT TTC TGG CAG CAG        3158
Ile Gly Pro Gly Thr Gly Ile Ala Pro Phe Arg Ser Phe Trp Gln Gln
            975                 980                 985

CGG CTC CAT GAC TCC CAG CAC AAA GGG CTC AAA GGA GGC CGC ATG AGC        3206
Arg Leu His Asp Ser Gln His Lys Gly Leu Lys Gly Gly Arg Met Ser
990                 995                 1000                1005

TTG GTG TTT GGG TGC CGG CAC CCG GAG GAG GAC CAC CTC TAT CAG GAA        3254
Leu Val Phe Gly Cys Arg His Pro Glu Glu Asp His Leu Tyr Gln Glu
                1010                1015                1020

GAA ATG CAG GAG ATG GTC CGC AAG AGA GTG CTG TTC CAG GTG CAC ACA        3302
Glu Met Gln Glu Met Val Arg Lys Arg Val Leu Phe Gln Val His Thr
                1025                1030                1035

GGC TAC TCC CGG CTG CCC GGC AAA CCC AAG GTC TAC GTT CAG GAC ATC        3350
Gly Tyr Ser Arg Leu Pro Gly Lys Pro Lys Val Tyr Val Gln Asp Ile
            1040                1045                1050

GTG CAA AAG CAG CTG GCC AAT GAG GTA CTC AGC GTG CTC CAC GGG GAG        3398
Val Gln Lys Gln Leu Ala Asn Glu Val Leu Ser Val Leu His Gly Glu
        1055                1060                1065

CAG GGC CAC CTC TAC ATT TGC GGA GAT GTG CGC ATG GCT CGG GAT GTG        3446
Gln Gly His Leu Tyr Ile Cys Gly Asp Val Arg Met Ala Arg Asp Val
1070                1075                1080                1085

GCT ACC ACA TTG AAG AAG CTG GTG GCC ACC AAG CTG AAC TTG AGC GAG        3494
Ala Thr Thr Leu Lys Lys Leu Val Ala Thr Lys Leu Asn Leu Ser Glu
            1090                1095                1100

GAG CAG GTG GAA GAC TAT TTC TTC CAG CTC AAG AGC CAG AAA CGT TAT        3542
Glu Gln Val Glu Asp Tyr Phe Phe Gln Leu Lys Ser Gln Lys Arg Tyr
            1105                1110                1115

CAT GAA GAT ATC TTC GGT GCA GTC TTT TCC TAT GGG GCA AAA AAG GGC        3590
His Glu Asp Ile Phe Gly Ala Val Phe Ser Tyr Gly Ala Lys Lys Gly
            1120                1125                1130

AGC GCC TTG GAG GAG CCC AAA GCC ACG AGG CTC TGACAGCCCA GAGTTCCAGC     3643
Ser Ala Leu Glu Glu Pro Lys Ala Thr Arg Leu
1135                1140
```

Fig. 1 continuation

```
TTCTGGCACT GAGTAAAGAT AATGGTGAGG GGCTTGGGGA GACAGCGAAA TGCAATCCCC    3703
CCCAAGCCCC TCATGTCATT CCCCCCTCCT CCACCCTACC AAGTAGTATT GTATTATTGT    3763
GGACTACTAA ATCTCTCTCC TCTCCTCCCT CCCCTCTCTC CCTTTCCTCC CTTCTTCTCC    3823
ACTCCCCAGC TCCCTCCTTC TCCTTCTCCT CCTTTGCCTC TCACTCTTCC TTGGAGCTGA    3883
GAGCAGAGAA AAACTCAACC TCCTGACTGA AGCACTTTGG GTCACCACCA GGAGGCACCA    3943
TGCCGCCGCT CTAATACTTA GCTGCACTAT GTACAGATAT TTATACTTCA TATTTAAGAA    4003
AACAGATACT TTTGTCTACT CCCAATGATG GCTTGGGCCT TTCCTGTATA ATTCCTTGAT    4063
GAAAAATATT TATATAAAAT ACATTTTATT TTAATCAAAA AAAAAAA                   4110
```

Fig. 2

```
GAGCGGACGG GCTCATGATG CCTCAGATCT GATCCGCATC TAACAGGCTG GCAATGAAGA          60

TACCCAGAGA ATAGTTCACA TCTATCATGC GTCACTTCTA GACACAGCCA TCAGACGCAT         120

CTCCTCCCCT TTCTGCCTGA CCTTAGGACA CGTCCCACCG CCTCTCTTGA CGTCTGCCTG         180

GTCAACCATC ACTTCCTTAG AGAATAAGGA GAGAGGCGGA TGCAGGAAAT CATGCCACCG         240

ACGGGCCACC AGCCATGAGT GGGTGACGCT GAGCTGACGT CAAAGACAGA GAGGGCTGAA         300

GCCTTGTCAG CACCTGTCAC CCCGGCTCCT GCTCTCCGTG TAGCCTGAAG CCTGGATCCT         360

CCTGGTGAAA TCATCTTGGC CTGATAGCAT TGTGAGGTCT TCAGACAGGA CCCCTCGGAA         420
```

| | | | | | | |
|---|---|---|---|---|---|---|
| GCTAGTTACC | ATG GAG GAT CAC ATG TTC GGT GTT CAG CAA ATC CAG CCC | | | | | 469 |
| | Met Glu Asp His Met Phe Gly Val Gln Gln Ile Gln Pro | | | | | |
| | 1145 | | 1150 | | 1155 | |

```
AAT GTC ATT TCT GTT CGT CTC TTC AAG CGC AAA GTT GGG GGC CTG GGA          517
Asn Val Ile Ser Val Arg Leu Phe Lys Arg Lys Val Gly Gly Leu Gly
         1160                1165                1170

TTT CTG GTG AAG GAG CGG GTC AGT AAG CCG CCC GTG ATC ATC TCT GAC          565
Phe Leu Val Lys Glu Arg Val Ser Lys Pro Pro Val Ile Ile Ser Asp
     1175                1180                1185

CTG ATT CGT GGG GGC GCC GCA GAG CAG AGT GGC CTC ATC CAG GCC GGA          613
Leu Ile Arg Gly Gly Ala Ala Glu Gln Ser Gly Leu Ile Gln Ala Gly
1190                1195                1200                1205

GAC ATC ATT CTT GCG GTC AAC GGC CGG CCC TTG GTG GAC CTG AGC TAT          661
Asp Ile Ile Leu Ala Val Asn Gly Arg Pro Leu Val Asp Leu Ser Tyr
             1210                1215                1220

GAC AGC GCC CTG GAG GTA CTC AGA GGC ATT GCC TCT GAG ACC CAC GTG          709
Asp Ser Ala Leu Glu Val Leu Arg Gly Ile Ala Ser Glu Thr His Val
         1225                1230                1235

GTC CTC ATT CTG AGG GGC CCT GAA GGT TTC ACC ACG CAC CTG GAG ACC          757
Val Leu Ile Leu Arg Gly Pro Glu Gly Phe Thr Thr His Leu Glu Thr
     1240                1245                1250

ACC TTT ACA GGT GAT GGG ACC CCC AAG ACC ATC CGG GTG ACA CAG CCC          805
Thr Phe Thr Gly Asp Gly Thr Pro Lys Thr Ile Arg Val Thr Gln Pro
1255                1260                1265

CTG GGT CCC CCC ACC AAA GCC GTG GAT CTG TCC CAC CAG CCA CCG GCC          853
Leu Gly Pro Pro Thr Lys Ala Val Asp Leu Ser His Gln Pro Pro Ala
1270                1275                1280                1285

GGC AAA GAA CAG CCC CTG GCA GTG GAT GGG GCC TCG GGT CCC GGG AAT          901
Gly Lys Glu Gln Pro Leu Ala Val Asp Gly Ala Ser Gly Pro Gly Asn
             1290                1295                1300

GGG CCT CAG CAT GCC TAC GAT GAT GGG CAG GAG GCT GGC TCA CTC CCC          949
Gly Pro Gln His Ala Tyr Asp Asp Gly Gln Glu Ala Gly Ser Leu Pro
         1305                1310                1315
```

Fig. 2 continuation

```
CAT GCC AAC GGC TGG CCC CAG GCC CCC AGG CAG GAC CCC GCG AAG AAA      997
His Ala Asn Gly Trp Pro Gln Ala Pro Arg Gln Asp Pro Ala Lys Lys
        1320                1325                1330

GCA ACC AGA GTC AGC CTC CAA GGC AGA GGG GAG AAC AAT GAA CTG CTC     1045
Ala Thr Arg Val Ser Leu Gln Gly Arg Gly Glu Asn Asn Glu Leu Leu
    1335                1340                1345

AAG GAG ATA GAG CCT GTG CTG AGC CTT CTC ACC AGT GGG AGC AGA GGG     1093
Lys Glu Ile Glu Pro Val Leu Ser Leu Leu Thr Ser Gly Ser Arg Gly
1350                1355                1360                1365

GTC AAG GGA GGG GCA CCT GCC AAG GCA GAG ATG AAA GAT ATG GGA ATC     1141
Val Lys Gly Gly Ala Pro Ala Lys Ala Glu Met Lys Asp Met Gly Ile
                1370                1375                1380

CAG GTG GAC AGA GAT TTG GAC GGC AAG TCA CAC AAA CCT CTG CCC CTC     1189
Gln Val Asp Arg Asp Leu Asp Gly Lys Ser His Lys Pro Leu Pro Leu
            1385                1390                1395

GGC GTG GAG AAC GAC CGA GTC TTC AAT GAC CTA TGG GGG AAG GGC AAT     1237
Gly Val Glu Asn Asp Arg Val Phe Asn Asp Leu Trp Gly Lys Gly Asn
        1400                1405                1410

GTG CCT GTC GTC CTC AAC AAC CCA TAT TCA GAG AAG GAG CAG CCC CCC     1285
Val Pro Val Val Leu Asn Asn Pro Tyr Ser Glu Lys Glu Gln Pro Pro
    1415                1420                1425

ACC TCA GGA AAA CAG TCC CCC ACA AAG AAT GGC AGC CCC TCC AAG TGT     1333
Thr Ser Gly Lys Gln Ser Pro Thr Lys Asn Gly Ser Pro Ser Lys Cys
1430                1435                1440                1445

CCA CGC TTC CTC AAG GTC AAG AAC TGG GAG ACT GAG GTG GTT CTC ACT     1381
Pro Arg Phe Leu Lys Val Lys Asn Trp Glu Thr Glu Val Val Leu Thr
                1450                1455                1460

GAC ACC CTC CAC CTT AAG AGC ACA TTG GAA ACG GGA TGC ACT GAG TAC     1429
Asp Thr Leu His Leu Lys Ser Thr Leu Glu Thr Gly Cys Thr Glu Tyr
            1465                1470                1475

ATC TGC ATG GGC TCC ATC ATG CAT CCT TCT CAG CAT GCA AGG AGG CCT     1477
Ile Cys Met Gly Ser Ile Met His Pro Ser Gln His Ala Arg Arg Pro
        1480                1485                1490

GAA GAC GTC CGC ACA AAA GGA CAG CTC TTC CCT CTC GCC AAA GAG TTT     1525
Glu Asp Val Arg Thr Lys Gly Gln Leu Phe Pro Leu Ala Lys Glu Phe
    1495                1500                1505

ATT GAT CAA TAC TAT TCA TCA ATT AAA AGA TTT GGC TCC AAA GCC CAC     1573
Ile Asp Gln Tyr Tyr Ser Ser Ile Lys Arg Phe Gly Ser Lys Ala His
1510                1515                1520                1525

ATG GAA AGG CTG GAA GAG GTG AAC AAA GAG ATC GAC ACC ACT AGC ACT     1621
Met Glu Arg Leu Glu Glu Val Asn Lys Glu Ile Asp Thr Thr Ser Thr
                1530                1535                1540

TAC CAG CTC AAG GAC ACA GAG CTC ATC TAT GGG GCC AAG CAC GCC TGG     1669
Tyr Gln Leu Lys Asp Thr Glu Leu Ile Tyr Gly Ala Lys His Ala Trp
            1545                1550                1555
```

Fig. 2 continuation

```
CGG AAT GCC TCG CGC TGT GTG GGC AGG ATC CAG TGG TCC AAG CTG CAG    1717
Arg Asn Ala Ser Arg Cys Val Gly Arg Ile Gln Trp Ser Lys Leu Gln
        1560            1565            1570

GTA TTC GAT GCC CGT GAC TGC ACC ACG GCC CAC GGG ATG TTC AAC TAC    1765
Val Phe Asp Ala Arg Asp Cys Thr Thr Ala His Gly Met Phe Asn Tyr
    1575            1580            1585

ATC TGT AAC CAT GTC AAG TAT GCC ACC AAC AAA GGG AAC CTC AGG TCT    1813
Ile Cys Asn His Val Lys Tyr Ala Thr Asn Lys Gly Asn Leu Arg Ser
1590            1595            1600            1605

GCC ATC ACC ATA TTC CCC CAG AGG ACA GAC GGC AAG CAC GAC TTC CGA    1861
Ala Ile Thr Ile Phe Pro Gln Arg Thr Asp Gly Lys His Asp Phe Arg
        1610            1615            1620

GTC TGG AAC TCC CAG CTC ATC CGC TAC GCT GGC TAC AAG CAC CGT GAC    1909
Val Trp Asn Ser Gln Leu Ile Arg Tyr Ala Gly Tyr Lys His Arg Asp
        1625            1630            1635

GGC TCC ACC CTG GGG GAC CCA GCC AAT GTG CAG TTC ACA GAG ATA TGC    1957
Gly Ser Thr Leu Gly Asp Pro Ala Asn Val Gln Phe Thr Glu Ile Cys
        1640            1645            1650

ATA CAG CAG GGC TGG AAA CCG CCT AGA GGC CGC TTC GAT GTC CTG CCG    2005
Ile Gln Gln Gly Trp Lys Pro Pro Arg Gly Arg Phe Asp Val Leu Pro
        1655            1660            1665

CTC CTG CTT CAG GCC AAC GGC AAT GAC CCT GAG CTC TTC CAG ATT CCT    2053
Leu Leu Leu Gln Ala Asn Gly Asn Asp Pro Glu Leu Phe Gln Ile Pro
1670            1675            1680            1685

CCA GAG CTG GTG TTG GAA CTT CCC ATC AGG CAC CCC AAG TTT GAG TGG    2101
Pro Glu Leu Val Leu Glu Leu Pro Ile Arg His Pro Lys Phe Glu Trp
        1690            1695            1700

TTC AAG GAC CTG GCG CTG AAG TGG TAC GGC CTC CCC GCC GTG TCC AAC    2149
Phe Lys Asp Leu Ala Leu Lys Trp Tyr Gly Leu Pro Ala Val Ser Asn
        1705            1710            1715

ATG CTC CTA GAG ATT GGC GGC CTG GAG TTC AGC GCC TGT CCC TTC AGT    2197
Met Leu Leu Glu Ile Gly Gly Leu Glu Phe Ser Ala Cys Pro Phe Ser
        1720            1725            1730

GGC TGG TAC ATG GGC ACA GAG ATT GGT GTC CGC GAC TAC TGT GAC AAC    2245
Gly Trp Tyr Met Gly Thr Glu Ile Gly Val Arg Asp Tyr Cys Asp Asn
        1735            1740            1745

TCC CGC TAC AAT ATC CTG GAG GAA GTG GCC AAG AAG ATG AAC TTA GAC    2293
Ser Arg Tyr Asn Ile Leu Glu Glu Val Ala Lys Lys Met Asn Leu Asp
1750            1755            1760            1765

ATG AGG AAG ACG TCC TCC CTG TGG AAG GAC CAG GCG CTG GTG GAG ATC    2341
Met Arg Lys Thr Ser Ser Leu Trp Lys Asp Gln Ala Leu Val Glu Ile
                1770            1775            1780

AAT ATC GCG GTT CTC TAT AGC TTC CAG AGT GAC AAA GTG ACC ATT GTT    2389
Asn Ile Ala Val Leu Tyr Ser Phe Gln Ser Asp Lys Val Thr Ile Val
        1785            1790            1795
```

Fig. 2 continuation

```
GAC CAT CAC TCC GCC ACC GAG TCC TTC ATT AAG CAC ATG GAG AAT GAG      2437
Asp His His Ser Ala Thr Glu Ser Phe Ile Lys His Met Glu Asn Glu
    1800                1805                1810

TAC CGC TGC CGG GGG GGC TGC CCT GCC GAC TGG GTG TGG ATC GTG CCC      2485
Tyr Arg Cys Arg Gly Gly Cys Pro Ala Asp Trp Val Trp Ile Val Pro
    1815                1820                1825

CCC ATG TCC GGA AGC ATC ACC CCT GTG TTC CAC CAG GAG ATG CTC AAC      2533
Pro Met Ser Gly Ser Ile Thr Pro Val Phe His Gln Glu Met Leu Asn
1830                1835                1840                1845

TAC CGG CTC ACC CCC TCC TTC GAA TAC CAG CCT GAT CCC TGG AAC ACG      2581
Tyr Arg Leu Thr Pro Ser Phe Glu Tyr Gln Pro Asp Pro Trp Asn Thr
                1850                1855                1860

CAT GTC TGG AAA GGC ACC AAC GGG ACC CCC ACA AAG CGG CGA GCC ATC      2629
His Val Trp Lys Gly Thr Asn Gly Thr Pro Thr Lys Arg Arg Ala Ile
            1865                1870                1875

GGC TTC AAG AAG CTA GCA GAA GCT GTC AAG TTC TCG GCC AAG CTG ATG      2677
Gly Phe Lys Lys Leu Ala Glu Ala Val Lys Phe Ser Ala Lys Leu Met
        1880                1885                1890

GGG CAG GCT ATG GCC AAG AGG GTG AAA GCG ACC ATC CTC TAT GCC ACA      2725
Gly Gln Ala Met Ala Lys Arg Val Lys Ala Thr Ile Leu Tyr Ala Thr
    1895                1900                1905

GAG ACA GGC AAA TCG CAA GCT TAT GCC AAG ACC TTG TGT GAG ATC TTC      2773
Glu Thr Gly Lys Ser Gln Ala Tyr Ala Lys Thr Leu Cys Glu Ile Phe
1910                1915                1920                1925

AAA CAC GCC TTT GAT GCC AAG GTG ATG TCC ATG GAA GAA TAT GAC ATT      2821
Lys His Ala Phe Asp Ala Lys Val Met Ser Met Glu Glu Tyr Asp Ile
                1930                1935                1940

GTG CAC CTG GAA CAT GAA ACT CTG GTC CTT GTG GTC ACC AGC ACC TTT      2869
Val His Leu Glu His Glu Thr Leu Val Leu Val Val Thr Ser Thr Phe
            1945                1950                1955

GGC AAT GGA GAT CCC CCT GAG AAT GGG GAG AAA TTC GGC TGT GCT TTG      2917
Gly Asn Gly Asp Pro Pro Glu Asn Gly Glu Lys Phe Gly Cys Ala Leu
        1960                1965                1970

ATG GAA ATG AGG CAC CCC AAC TCT GTG CAG GAA GAA AGG AAG AGC TAC      2965
Met Glu Met Arg His Pro Asn Ser Val Gln Glu Glu Arg Lys Ser Tyr
    1975                1980                1985

AAG GTC CGA TTC AAC AGC GTC TCC TCC TAC TCT GAC TCC CAA AAA TCA      3013
Lys Val Arg Phe Asn Ser Val Ser Ser Tyr Ser Asp Ser Gln Lys Ser
1990                1995                2000                2005

TCA GGC GAT GGG CCC GAC CTC AGA GAC AAC TTT GAG AGT GCT GGA CCC      3061
Ser Gly Asp Gly Pro Asp Leu Arg Asp Asn Phe Glu Ser Ala Gly Pro
                2010                2015                2020

CTG GCC AAT GTG AGG TTC TCA GTT TTT GGC CTC GGC TCA CGA GCA TAC      3109
Leu Ala Asn Val Arg Phe Ser Val Phe Gly Leu Gly Ser Arg Ala Tyr
            2025                2030                2035
```

Fig. 2 continuation

```
CCT CAC TTT TGC GCC TTC GGA CAC GCT GTG GAC ACC CTC CTG GAA GAA        3157
Pro His Phe Cys Ala Phe Gly His Ala Val Asp Thr Leu Leu Glu Glu
        2040                    2045                    2050

CTG GGA GGG GAG AGG ATC CTG AAG ATG AGG GAA GGG GAT GAG CTC TGT        3205
Leu Gly Gly Glu Arg Ile Leu Lys Met Arg Glu Gly Asp Glu Leu Cys
        2055                    2060                    2065

GGG CAG GAA GAG GCT TTC AGG ACC TGG GCC AAG AAG GTC TTC AAG GCA        3253
Gly Gln Glu Glu Ala Phe Arg Thr Trp Ala Lys Lys Val Phe Lys Ala
2070                    2075                    2080            2085

GCC TGT GAT GTC TTC TGT GTG GGA GAT GAT GTC AAC ATT GAA AAG GCC        3301
Ala Cys Asp Val Phe Cys Val Gly Asp Asp Val Asn Ile Glu Lys Ala
                2090                    2095                    2100

AAC AAT TCC CTC ATC AGC AAT GAT CGC AGC TGG AAG AGA AAC AAG TTC        3349
Asn Asn Ser Leu Ile Ser Asn Asp Arg Ser Trp Lys Arg Asn Lys Phe
                2105                    2110                    2115

CGC CTC ACC TTT GTG GCC GAA GCT CCA GAA CTC ACA CAA GGT CTA TCC        3397
Arg Leu Thr Phe Val Ala Glu Ala Pro Glu Leu Thr Gln Gly Leu Ser
        2120                    2125                    2130

AAT GTC CAC AAA AAG CGA GTC TCA GCT GCC CGG CTC CTT AGC CGT CAA        3445
Asn Val His Lys Lys Arg Val Ser Ala Ala Arg Leu Leu Ser Arg Gln
        2135                    2140                    2145

AAC CTC CAG AGC CCT AAA TCC AGT CGG TCA ACT ATC TTC GTG CGT CTC        3493
Asn Leu Gln Ser Pro Lys Ser Ser Arg Ser Thr Ile Phe Val Arg Leu
2150                    2155                    2160            2165

CAC ACC AAC GGG AGC CAG GAG CTG CAG TAC CAG CCT GGG GAC CAC CTG        3541
His Thr Asn Gly Ser Gln Glu Leu Gln Tyr Gln Pro Gly Asp His Leu
                2170                    2175                    2180

GGT GTC TTC CCT GGC AAC CAC GAG GAC CTC GTG AAT GCC CTG ATC GAG        3589
Gly Val Phe Pro Gly Asn His Glu Asp Leu Val Asn Ala Leu Ile Glu
                2185                    2190                    2195

CGG CTG GAG GAC GCG CCG CCT GTC AAC CAG ATG GTG AAA GTG GAA CTG        3637
Arg Leu Glu Asp Ala Pro Pro Val Asn Gln Met Val Lys Val Glu Leu
                2200                    2205                    2210

CTG GAG GAG CGG AAC ACG GCT TTA GGT GTC ATC AGT AAC TGG ACA GAC        3685
Leu Glu Glu Arg Asn Thr Ala Leu Gly Val Ile Ser Asn Trp Thr Asp
        2215                    2220                    2225

GAG CTC CGC CTC CCG CCC TGC ACC ATC TTC CAG GCC TTC AAG TAC TAC        3733
Glu Leu Arg Leu Pro Pro Cys Thr Ile Phe Gln Ala Phe Lys Tyr Tyr
2230                    2235                    2240            2245

CTG GAC ATC ACC ACG CCA CCA ACG CCT CTG CAG CTG CAG CAG TTT GCC        3781
Leu Asp Ile Thr Thr Pro Pro Thr Pro Leu Gln Leu Gln Gln Phe Ala
                2250                    2255                    2260

TCC CTA GCT ACC AGC GAG AAG GAG AAG CAG CGT CTG CTG GTC CTC AGC        3829
Ser Leu Ala Thr Ser Glu Lys Glu Lys Gln Arg Leu Leu Val Leu Ser
        2265                    2270                    2275
```

Fig. 2 continuation

```
AAG GGT TTG CAG GAG TAC GAG GAA TGG AAA TGG GGC AAG AAC CCC ACC         3877
Lys Gly Leu Gln Glu Tyr Glu Glu Trp Lys Trp Gly Lys Asn Pro Thr
        2280                2285                2290

ATC GTG GAG GTG CTG GAG GAG TTC CCA TCT ATC CAG ATG CCG GCC ACC         3925
Ile Val Glu Val Leu Glu Glu Phe Pro Ser Ile Gln Met Pro Ala Thr
        2295                2300                2305

CTG CTC CTG ACC CAG CTG TCC CTG CTG CAG CCC CGC TAC TAT TCC ATC         3973
Leu Leu Leu Thr Gln Leu Ser Leu Leu Gln Pro Arg Tyr Tyr Ser Ile
2310                2315                2320                2325

AGC TCC TCC CCA GAC ATG TAC CCT GAT GAA GTG CAC CTC ACT GTG GCC         4021
Ser Ser Ser Pro Asp Met Tyr Pro Asp Glu Val His Leu Thr Val Ala
                2330                2335                2340

ATC GTT TCC TAC CGC ACT CGA GAT GGA GAA GGA CCA ATT CAC CAC GGC         4069
Ile Val Ser Tyr Arg Thr Arg Asp Gly Glu Gly Pro Ile His His Gly
            2345                2350                2355

GTA TGC TCC TCC TGG CTC AAC CGG ATA CAG GCT GAC GAA CTG GTC CCC         4117
Val Cys Ser Ser Trp Leu Asn Arg Ile Gln Ala Asp Glu Leu Val Pro
        2360                2365                2370

TGT TTC GTG AGA GGA GCA CCC AGC TTC CAC CTG CCC CGG AAC CCC CAA         4165
Cys Phe Val Arg Gly Ala Pro Ser Phe His Leu Pro Arg Asn Pro Gln
    2375                2380                2385

GTC CCC TGC ATC CTC GTT GGA CCA GGC ACC GGC ATT GCC CCT TTC CGA         4213
Val Pro Cys Ile Leu Val Gly Pro Gly Thr Gly Ile Ala Pro Phe Arg
2390                2395                2400                2405

AGC TTC TGG CAA CAG CGG CAA TTT GAT ATC CAA CAC AAA GGA ATG AAC         4261
Ser Phe Trp Gln Gln Arg Gln Phe Asp Ile Gln His Lys Gly Met Asn
                2410                2415                2420

CCC TGC CCC ATG GTC CTG GTC TTC GGG TGC CGG CAA TCC AAG ATA GAT         4309
Pro Cys Pro Met Val Leu Val Phe Gly Cys Arg Gln Ser Lys Ile Asp
            2425                2430                2435

CAT ATC TAC AGG GAA GAG ACC CTG CAG GCC AAG AAC AAG GGG GTC TTC         4357
His Ile Tyr Arg Glu Glu Thr Leu Gln Ala Lys Asn Lys Gly Val Phe
        2440                2445                2450

AGA GAG CTG TAC ACG GCT TAC TCC CGG GAG CCA GAC AAA CCA AAG AAG         4405
Arg Glu Leu Tyr Thr Ala Tyr Ser Arg Glu Pro Asp Lys Pro Lys Lys
    2455                2460                2465

TAC GTG CAG GAC ATC CTG CAG GAG CAG CTG GCG GAG TCT GTG TAC CGA         4453
Tyr Val Gln Asp Ile Leu Gln Glu Gln Leu Ala Glu Ser Val Tyr Arg
2470                2475                2480                2485

GCC CTG AAG GAG CAA GGG GGC CAC ATA TAC GTC TGT GGG GAC GTC ACC         4501
Ala Leu Lys Glu Gln Gly Gly His Ile Tyr Val Cys Gly Asp Val Thr
                2490                2495                2500

ATG GCT GCT GAT GTC CTC AAA GCC ATC CAG CGC ATC ATG ACC CAG CAG         4549
Met Ala Ala Asp Val Leu Lys Ala Ile Gln Arg Ile Met Thr Gln Gln
            2505                2510                2515
```

Fig. 2 continuation

```
GGG AAG CTC TCG GCA GAG GAC GCC GGC GTA TTC ATC AGC CGG ATG AGG        4597
Gly Lys Leu Ser Ala Glu Asp Ala Gly Val Phe Ile Ser Arg Met Arg
        2520            Ala Glu Asp    2525            Ser Arg Met Arg
                                                        2530

GAT GAC AAC CGA TAC CAT GAG GAT ATT TTT GGA GTC ACC CTG CGA ACG        4645
Asp Asp Asn Arg Tyr His Glu Asp Ile Phe Gly Val Thr Leu Arg Thr
        2535            2540                    2545

ATC GAA GTG ACC AAC CGC CTT AGA TCT GAG TCC ATT GCC TTC ATT GAA        4693
Ile Glu Val Thr Asn Arg Leu Arg Ser Glu Ser Ile Ala Phe Ile Glu
2550            2555                    2560                    2565

GAG AGC AAA AAA GAC ACC GAT GAG GTT TTC AGC TCC TAACTGGACC             4739
Glu Ser Lys Lys Asp Thr Asp Glu Val Phe Ser Ser
            2570            2575

CTCTTGCCCA GCCGGCTGCA AGTTTGTAAG CGCGGGACAG A                          4780
```

Fig. 3

```
                GAATTCGGCA CGAGGAGCCA CAGAGCAGAC GGAGGCCGCC CGTCCGGCCC CAGCGAC              57

ATG GGC AAC TTG AAG AGT GTG GGC CAG GAG CCC GGG CCC CCC TGC GGC                          105
Met Gly Asn Leu Lys Ser Val Gly Gln Glu Pro Gly Pro Pro Cys Gly
    1435            1440                1445

CTG GGG CTG GGG CTG GGC CTC GGG CTA TGC GGC AAG CAG GGC CCA GCC                          153
Leu Gly Leu Gly Leu Gly Leu Gly Leu Cys Gly Lys Gln Gly Pro Ala
1450            1455                1460                    1465

TCC CCG GCA CCT GAG CCC AGC CGG GCC CCC GCA CCC GCC ACC CCG CAC                          201
Ser Pro Ala Pro Glu Pro Ser Arg Ala Pro Ala Pro Ala Thr Pro His
                1470                1475                1480

GCG CCA GAC CAC AGC CCA GCT CCC AAC AGC CCC ACG CTG ACC CGG CCT                          249
Ala Pro Asp His Ser Pro Ala Pro Asn Ser Pro Thr Leu Thr Arg Pro
            1485                1490                1495

CCG GAG GGG CCC AAG TTC CCT CGC GTG AAG AAC TGG GAG CTG GGG AGC                          297
Pro Glu Gly Pro Lys Phe Pro Arg Val Lys Asn Trp Glu Leu Gly Ser
        1500                1505                1510

ATC ACC TAC GAC ACT CTG TGC GCG CAG TCC CAA CAG GAC GGG CCC TGC                          345
Ile Thr Tyr Asp Thr Leu Cys Ala Gln Ser Gln Gln Asp Gly Pro Cys
    1515                1520                1525

ACT CCC AGG CGC TGC CTG GGC TCC CTG GTG TTG CCC CGG AAA CTG CAG                          393
Thr Pro Arg Arg Cys Leu Gly Ser Leu Val Leu Pro Arg Lys Leu Gln
1530                1535                1540                    1545

ACC CGG CCC TCC CCG GGA CCT CCA CCC GCT GAG CAG CTG CTG AGC CAG                          441
Thr Arg Pro Ser Pro Gly Pro Pro Pro Ala Glu Gln Leu Leu Ser Gln
                1550                1555                1560

GCC AGG GAC TTC ATC AAC CAG TAC TAC AGC TCC ATC AAG AGG AGC GGC                          489
Ala Arg Asp Phe Ile Asn Gln Tyr Tyr Ser Ser Ile Lys Arg Ser Gly
            1565                1570                1575

TCC CAG GCT CAC GAG GAG CGG CTT CAG GAG GTG GAG GCC GAG GTG GCA                          537
Ser Gln Ala His Glu Glu Arg Leu Gln Glu Val Glu Ala Glu Val Ala
        1580                1585                1590

TCC ACG GGC ACC ATC CAC CTC CGA GAG AGT GAG CTG GTG TTC GGG GCC                          585
Ser Thr Gly Thr Ile His Leu Arg Glu Ser Glu Leu Val Phe Gly Ala
    1595                1600                1605

AAG CAG GCC TGG CGC AAT GCA CCC CGC TGC GTG GGC CGC ATC CAG TGG                          633
Lys Gln Ala Trp Arg Asn Ala Pro Arg Cys Val Gly Arg Ile Gln Trp
1610            1615                1620                    1625

GGG AAG CTG CAG GTG TTT GAT GCC CGG GAC TGC AGC TCA GCA CAG GAG                          681
Gly Lys Leu Gln Val Phe Asp Ala Arg Asp Cys Ser Ser Ala Gln Glu
                1630                1635                1640

ATG TTC ACC TAC ATC TGC AAC CAC ATC AAG TAC GCC ACC AAC CGC GGC                          729
Met Phe Thr Tyr Ile Cys Asn His Ile Lys Tyr Ala Thr Asn Arg Gly
            1645                1650                1655
```

Fig. 3 continuation

```
AAC CTT CGC TCG GCC ATC ACA GTG TTC CCG CAG CGC GCC CCG GGC CGC      777
Asn Leu Arg Ser Ala Ile Thr Val Phe Pro Gln Arg Ala Pro Gly Arg
    1660            1665                1670

GGA GAC TTC CGG ATC TGG AAC AGC CAG CTG GTG CGC TAC GCA GGC TAC      825
Gly Asp Phe Arg Ile Trp Asn Ser Gln Leu Val Arg Tyr Ala Gly Tyr
    1675            1680                1685

AGA CAG CAG GAT GGC TCT GTG CGT GGG GAC CCA GCC AAC GTG GAG ATC      873
Arg Gln Gln Asp Gly Ser Val Arg Gly Asp Pro Ala Asn Val Glu Ile
1690            1695                1700                1705

ACG GAG CTC TGC ATC CAG CAC GGC TGG ACC CCC GGA AAC GGC CGC TTC      921
Thr Glu Leu Cys Ile Gln His Gly Trp Thr Pro Gly Asn Gly Arg Phe
                1710                1715                1720

GAC GTG CTG CCC CTG CTC CTC CAG GCC CCA GAC GAG GCT CCA GAG CTC      969
Asp Val Leu Pro Leu Leu Leu Gln Ala Pro Asp Glu Ala Pro Glu Leu
            1725                1730                1735

TTT GTT CTG CCC CCC GAG CTG GTC CTT GAA GTG CCC CTA GGA GCA CCC     1017
Phe Val Leu Pro Pro Glu Leu Val Leu Glu Val Pro Leu Gly Ala Pro
        1740                1745                1750

CAC ACT GGA GTG GTT CGC GGC CCT GGG CTG CGA TGG TAT GCC CTC CCG     1065
His Thr Gly Val Val Arg Gly Pro Gly Leu Arg Trp Tyr Ala Leu Pro
        1755                1760                1765

GCC GTG TCC AAC ATG CTG CTG GAA ATC GGG GGT CTG GAG TTC TCC GCG     1113
Ala Val Ser Asn Met Leu Leu Glu Ile Gly Gly Leu Glu Phe Ser Ala
1770                1775                1780                1785

GCC CCC TTC AGC GGC TGG TAC ATG AGC ACG GAG ATT GGC ACG CGG AAC     1161
Ala Pro Phe Ser Gly Trp Tyr Met Ser Thr Glu Ile Gly Thr Arg Asn
            1790                1795                1800

CTG TGT GAC CCT CAC CGC TAC AAT ATC CTG GAG GAT GTG GCC GTC TGC     1209
Leu Cys Asp Pro His Arg Tyr Asn Ile Leu Glu Asp Val Ala Val Cys
                1805                1810                1815

ATG GAC CTC GAC ACG CGG ACC ACC TCG TCC CTG TGG AAG GAC AAG GCG     1257
Met Asp Leu Asp Thr Arg Thr Thr Ser Ser Leu Trp Lys Asp Lys Ala
            1820                1825                1830

GCC GTG GAG ATC AAC CTG GCT GTG CTG CAC AGC TTT CAG CTC GCC AAG     1305
Ala Val Glu Ile Asn Leu Ala Val Leu His Ser Phe Gln Leu Ala Lys
    1835                1840                1845

GTG ACC ATC GTG GAC CAC CAC GCC GCC ACG GTG TCC TTC ATG AAG CAC     1353
Val Thr Ile Val Asp His His Ala Ala Thr Val Ser Phe Met Lys His
1850            1855                1860                1865

CTG GAC AAC GAG CAG AAG GCC AGG GGG GGC TGC CCC GCC GAC TGG GCC     1401
Leu Asp Asn Glu Gln Lys Ala Arg Gly Gly Cys Pro Ala Asp Trp Ala
            1870                1875                1880

TGG ATC GTG CCC CCC ATC TAC GGC AGC CTA CCG CCC GTC TTC CAC CAG     1449
Trp Ile Val Pro Pro Ile Tyr Gly Ser Leu Pro Pro Val Phe His Gln
        1885                1890                1895
```

Fig. 3 continuation

```
GAG ATG GTC AAC TAC ATC CTG TCC CCT GCC TTC CGC TAC CAG CCA GAC          1497
Glu Met Val Asn Tyr Ile Leu Ser Pro Ala Phe Arg Tyr Gln Pro Asp
        1900            1905            1910

CCC TGG AAA GGG AGC GCG ACC AAG GGC GCC GGC ATC ACC AGG AAG AAG          1545
Pro Trp Lys Gly Ser Ala Thr Lys Gly Ala Gly Ile Thr Arg Lys Lys
    1915            1920            1925

ACC TTT AAG GAA GTG GCC AAC GCG GTG AAG ATC TCT GCC TCA CTC ATG          1593
Thr Phe Lys Glu Val Ala Asn Ala Val Lys Ile Ser Ala Ser Leu Met
1930            1935            1940            1945

GGC ACC CTG ATG GCC AAG CGA GTG AAA GCA ACC ATC CTG TAC GCC TCT          1641
Gly Thr Leu Met Ala Lys Arg Val Lys Ala Thr Ile Leu Tyr Ala Ser
                1950            1955            1960

GAG ACC GGC CGG GCC CAG AGC TAC GCT CAG CAG CTG GGG AGG CTC TTC          1689
Glu Thr Gly Arg Ala Gln Ser Tyr Ala Gln Gln Leu Gly Arg Leu Phe
            1965            1970            1975

CGG AAG GCC TTC GAT CCC CGG GTC CTG TGC ATG GAT GAG TAT GAC GTG          1737
Arg Lys Ala Phe Asp Pro Arg Val Leu Cys Met Asp Glu Tyr Asp Val
        1980            1985            1990

GTG TCC CTG GAG CAC GAG GCA CTG GTG CTG GTG GTG ACC AGC ACC TTT          1785
Val Ser Leu Glu His Glu Ala Leu Val Leu Val Val Thr Ser Thr Phe
    1995            2000            2005

GGG AAT GGC GAT CCC CCG GAG AAT GGA GAG AGT TTT GCA GCT GCC CTG          1833
Gly Asn Gly Asp Pro Pro Glu Asn Gly Glu Ser Phe Ala Ala Ala Leu
2010            2015            2020            2025

ATG GAG ATG TCG GGG CCC TAC AAC AGC TCC CCA CGG CCG GAA CAG CAC          1881
Met Glu Met Ser Gly Pro Tyr Asn Ser Ser Pro Arg Pro Glu Gln His
                2030            2035            2040

AAG AGT TAC AAG ATC CGC TTC AAC AGC GTC TCC TGC TCA GAC CCG CTG          1929
Lys Ser Tyr Lys Ile Arg Phe Asn Ser Val Ser Cys Ser Asp Pro Leu
            2045            2050            2055

GTG TCC TCC TGG CGG CGG AAG AGA AAG GAG TCC AGC AAC ACA GAC AGC          1977
Val Ser Ser Trp Arg Arg Lys Arg Lys Glu Ser Ser Asn Thr Asp Ser
        2060            2065            2070

GCG GGG GCC CTG GGG ACC CTC AGG TTC TGT GTG TTC GGA CTG GGC TCC          2025
Ala Gly Ala Leu Gly Thr Leu Arg Phe Cys Val Phe Gly Leu Gly Ser
    2075            2080            2085

CGG GCG TAC CCC CAC TTC TGC GCC TTC GCG CGA GCG GTG GAC ACC CGG          2073
Arg Ala Tyr Pro His Phe Cys Ala Phe Ala Arg Ala Val Asp Thr Arg
2090            2095            2100            2105

CTG GAA GAG CTT GGA GGG GAG CGG CTG CTG CAG CTG GGC CAG GGC GAT          2121
Leu Glu Glu Leu Gly Gly Glu Arg Leu Leu Gln Leu Gly Gln Gly Asp
                2110            2115            2120

GAG CTC TGC GGC CAG GAA GAG GCC TTC CGT GGT TGG GCA AAG GCG GCA          2169
Glu Leu Cys Gly Gln Glu Glu Ala Phe Arg Gly Trp Ala Lys Ala Ala
            2125            2130            2135
```

Fig. 3 continuation

```
TTC CAG GCC TCC TGC GAG ACG TTC TGC GTT GGG GAG GAG GCC AAG GCT         2217
Phe Gln Ala Ser Cys Glu Thr Phe Cys Val Gly Glu Glu Ala Lys Ala
        2140                2145                2150

GCT GCC CAG GAC ATC TTC AGC CCC AAA CGG AGC TGG AAA CGC CAG AGG         2265
Ala Ala Gln Asp Ile Phe Ser Pro Lys Arg Ser Trp Lys Arg Gln Arg
    2155                2160                2165

TAC CGG CTG AGC GCC CAG GCC GAG GGC CTC CAG CTG CTG CCA GGC CTG         2313
Tyr Arg Leu Ser Ala Gln Ala Glu Gly Leu Gln Leu Leu Pro Gly Leu
2170                2175                2180                2185

ATC CAC GTG CAC AGA CGG AAG ATG TTT CAG GCC ACA GTC CTC TCG GTG         2361
Ile His Val His Arg Arg Lys Met Phe Gln Ala Thr Val Leu Ser Val
                2190                2195                2200

GAA AAT CTG CAA AGC AGC AAG TCC ACC CGG GCC ACC ATC CTG GTG CGC         2409
Glu Asn Leu Gln Ser Ser Lys Ser Thr Arg Ala Thr Ile Leu Val Arg
                2205                2210                2215

CTG GAC ACT GCA GGC CAG GAG GGG CTG CAG TAC CAG CCG GGG GAC CAC         2457
Leu Asp Thr Ala Gly Gln Glu Gly Leu Gln Tyr Gln Pro Gly Asp His
        2220                2225                2230

ATA GGC ATC TCC GCG CCC AAC CGG CCG GGC CTG GTG GAG GCG CTG CTG         2505
Ile Gly Ile Ser Ala Pro Asn Arg Pro Gly Leu Val Glu Ala Leu Leu
    2235                2240                2245

AGC CGC GTG GAG GAC CCG CCA CCG CCC ACC GAG TCT GTG GCT GTG GAG         2553
Ser Arg Val Glu Asp Pro Pro Pro Pro Thr Glu Ser Val Ala Val Glu
2250                2255                2260                2265

CAG CTG GAG AAA GGC AGC CCA GGC GGC CCT CCT CCC AGC TGG GTG CGG         2601
Gln Leu Glu Lys Gly Ser Pro Gly Gly Pro Pro Pro Ser Trp Val Arg
                2270                2275                2280

GAC CCA CGG CTG CCC CCG TGC ACC GTG CGC CAG GCT CTC ACC TTC TTC         2649
Asp Pro Arg Leu Pro Pro Cys Thr Val Arg Gln Ala Leu Thr Phe Phe
                2285                2290                2295

CTG GAC ATC ACC TCC CCA CCC AGC CCC CGG CTT CTC CGA CTG CTC AGC         2697
Leu Asp Ile Thr Ser Pro Pro Ser Pro Arg Leu Leu Arg Leu Leu Ser
        2300                2305                2310

ACC CTG GCC GAA GAA CCC AGC GAG CAG CAG GAG CTT GAG ACC CTC AGT         2745
Thr Leu Ala Glu Glu Pro Ser Glu Gln Gln Glu Leu Glu Thr Leu Ser
    2315                2320                2325

CAG GAC CCC CGG CGC TAC GAG GAG TGG AAG TTG GTC CGC TGC CCC ACG         2793
Gln Asp Pro Arg Arg Tyr Glu Glu Trp Lys Leu Val Arg Cys Pro Thr
2330                2335                2340                2345

CTG CTG GAG GTG CTG GAG CAG TTC CCG TCC GTG GCG CTG CCC GCC CCG         2841
Leu Leu Glu Val Leu Glu Gln Phe Pro Ser Val Ala Leu Pro Ala Pro
                2350                2355                2360

CTG CTC CTC ACC CAG CTG CCC CTG CTG CAG CCC CGG TAC TAC TCT GTC         2889
Leu Leu Leu Thr Gln Leu Pro Leu Leu Gln Pro Arg Tyr Tyr Ser Val
                2365                2370                2375
```

Fig. 3 continuation

```
AGC TCG GCC CCC AAC GCC CAC CCC GGA GAG GTC CAC CTC ACA GTG GCC     2937
Ser Ser Ala Pro Asn Ala His Pro Gly Glu Val His Leu Thr Val Ala
        2380            2385                2390

GTG CTG GCG TAC AGG ACC CAA GAT GGG CTG GGC CCC CTA CAC TAC GGG     2985
Val Leu Ala Tyr Arg Thr Gln Asp Gly Leu Gly Pro Leu His Tyr Gly
    2395            2400                2405

GTC TGC TCC ACA TGG CTG AGC CAG CTC AAG ACT GGA GAC CCC GTG CCC     3033
Val Cys Ser Thr Trp Leu Ser Gln Leu Lys Thr Gly Asp Pro Val Pro
2410            2415            2420            2425

TGC TTC ATC AGG GGG GCT CCC TCC TTC CGG CTG CCG CCT GAC CCC TAC     3081
Cys Phe Ile Arg Gly Ala Pro Ser Phe Arg Leu Pro Pro Asp Pro Tyr
            2430            2435            2440

GTG CCC TGC ATC CTC GTG GGC CCT GGC ACT GGC ATC GCC CCC TTC CGG     3129
Val Pro Cys Ile Leu Val Gly Pro Gly Thr Gly Ile Ala Pro Phe Arg
        2445            2450            2455

GGA TTT TGG CAG GAG AGG CTG CAT GAC ATT GAG AGC AAA GGG CTG CAG     3177
Gly Phe Trp Gln Glu Arg Leu His Asp Ile Glu Ser Lys Gly Leu Gln
    2460            2465            2470

CCG CAC CCC ATG ACC CTG GTG TTC GGC TGC CGC TGC TCC CAA CTC GAC     3225
Pro His Pro Met Thr Leu Val Phe Gly Cys Arg Cys Ser Gln Leu Asp
        2475            2480            2485

CAT CTC TAC CGC GAC GAG GTG CAG GAC GCC CAG GAG CGC GGG GTG TTT     3273
His Leu Tyr Arg Asp Glu Val Gln Asp Ala Gln Glu Arg Gly Val Phe
2490            2495            2500            2505

GGC CGC GTC CTC ACC GCC TTC TCC CGG GAA CCT GAC AGC CCC AAG ACC     3321
Gly Arg Val Leu Thr Ala Phe Ser Arg Glu Pro Asp Ser Pro Lys Thr
            2510            2515            2520

TAC GTA CAG GAC ATC CTG AGA ACC GAG CTG GCT GCC GAG GTG CAC CGC     3369
Tyr Val Gln Asp Ile Leu Arg Thr Glu Leu Ala Ala Glu Val His Arg
        2525            2530            2535

GTG CTG TGC CTC GAG CGG GGC CAC ATG TTT GTC TGC GGC GAT GTC ACT     3417
Val Leu Cys Leu Glu Arg Gly His Met Phe Val Cys Gly Asp Val Thr
    2540            2545            2550

ATG GCA ACC AGC GTC CTG CAG ACG GTG CAG CGC ATC TTG GCG ACA GAG     3465
Met Ala Thr Ser Val Leu Gln Thr Val Gln Arg Ile Leu Ala Thr Glu
        2555            2560            2565

GGC GAC ATG GAG CTG GAC GAG GCG GGC GAC GTC ATC GGC GTG CTG CGG     3513
Gly Asp Met Glu Leu Asp Glu Ala Gly Asp Val Ile Gly Val Leu Arg
2570            2575            2580            2585

GAT CAG CAA CGC TAT CAC GAG GAC ATT TTC GGC CTC ACG CTG CGC ACC     3561
Asp Gln Gln Arg Tyr His Glu Asp Ile Phe Gly Leu Thr Leu Arg Thr
            2590            2595            2600

CAG GAG GTG ACA AGC CGT ATA CGT ACC CAG AGC TTT TCC CTG CAG GAG     3609
Gln Glu Val Thr Ser Arg Ile Arg Thr Gln Ser Phe Ser Leu Gln Glu
        2605            2610            2615
```

Fig. 3 continuation

```
CGG CAT CTG CGG GGC GCG GTG CCC TGG GCC TTC GAC CCG CCC GGC CCA         3657
Arg His Leu Arg Gly Ala Val Pro Trp Ala Phe Asp Pro Pro Gly Pro
        2620                2625                2630

GAC ACC CCC GGC CCC TGAGACCCCT CTTGCTTCCC ACTGCAGTTC CCGGAGAGAG         3712
Asp Thr Pro Gly Pro
    2635

GGGCTGTCAT TCCACTATGG CTCTACCGCT GTCCTGTTGG CCTTTACCGG GACCGGCCAC       3772

CTCTCCCTCC CCTCCCAAGG TGACTTCCCA GAGACTGTTG GATTCCCTGT ACTATCTCAT       3832

CCTCTCATCT CTAGGTCTGT TTCCCCACCC TAAGTCCATC TGGAAGACCC CTCCCAGCAG       3892

CGGTATTCCA GAGCCTACAG TCAGCCCTTT GGTGTTTAGG TGAATTTTAG ATTCCCCTCG       3952

CCTCTCTCCC GGGAAGTATC TTATCTTGAA ACCTGATCTC TAAATCATTC AAATATTTAT       4012

TATTGAAGAT TTACCATAAG AGACTGGACC AGAAGTTAGG AGACCTACTA AGATGCCTAA       4072

GCCAAGGTCC TCCGGGGCCG AATTC                                            4097
``` pSP65h-CMV1 (2166 bps)

PSCT GALX-556      (2802 bps)

DNA EXPRESSION VECTORS FOR USE IN THE GENE THERAPEUTIC TREATMENT OF VASCULAR DISORDERS

CROSS REFERENCE TO RELATED APPLICATIONS

This is a continuation application of Ser. No. 08/553,503 filed Mar. 1, 1996, now abandoned, which is the national phase application of PCT/EP95/01202 filed Mar. 31, 1995 claiming priority of German Application P44 11 402.8 filed Mar. 31, 1994. The subject matter of each of these applications is hereby incorporated by reference.

The invention relates to the use of DNA expression vectors for gene therapeutic treatment of vascular disorders such as high blood pressure, arteriosclerosis, stenosis or restenosis.

BACKGROUND OF THE INVENTION

As percutaneous, transluminal coronary angioplasty (PTCA), one understands a method which is widely employed in the clinic in which the critical constriction of a coronary vessel (coronary stenosis) is mechanically dilated by a catheter and therewith made free again. To this day, the Achilles heal of PTCA is restenosis. This appears after weeks or months after successful PTCA in 12–43% of all treated patients (Lange, R.A. et al., Southwestern Internal Medicine Conference: Restenosis: The Achilles heal of coronary angioplasty, Am. J. Med. Sci., 265–274, 1993). A renewed PTCA or a bypass operation is the necessary consequence.

In the final analysis, the exact mechanism of restenosis is unexplained. However, of importance is the initial mechanical stretching stimulus in which, aside from destruction of the endothelial cells, tearing occurs in the arteriosclerotic wall region with simultaneous deposition of fibrin and blood platelets. The blood platelets on their part release vessel constricting and proliferation increasing metabolic products which veil the growth inhibiting factors of the smooth vessel musculature. A hyperplasty of the muscle media, i.e. restenosis, is the result.

Various strategies for the treatment of restenosis were examined in clinical studies in the past. Concerning pharmacological therapy, neither the use of anti-thrombotic agents (aspirin, heparin), antispastic agents (nifedipin, diltazem) or anliproliferative agents (colchicine) nor a lipid level sinking therapy had a favorable influence on the development of the restenosis. The development of new catheters for the minimalisation of tissue trauma (laser angioplasty, atherectomy catheter) has also brought no success in the prevention of restenosis.

There is no therapy for restenosis at the present. The reason is probably because the effective levels in blood after systemic application of a drug are too low to be able to be locally therapeutically effective.

Nitrogen monoxide (NO) is formed in mammalian cells from the amino acid L-arginine through the mediation of the enzyme NO synthase (NOS). NO is an important messenger substance and/or signal molecule in the human body which mediates a multitude of physiological and pathophysiological effects. In the central nervous system, NO is probably involved in the regulation of integrative performance, i.e. memory functions. In the gastrointestinal tract, an involvement in peristalsis is suspected. The NO formed by macrophages is capable of killing bacteria and parasites. Within the heart-circulatory system, NO is formed from the endothelial cells where it carries out two important functions. In the direction of the luminal side of the vessel it inhibits platelet aggregation and is therewith jointly responsible for the antithrombogenic properties of the vessel inner wall. On the side away from the lumen NO relaxes the smooth musculature and carries out a long-term proliferation inhibiting effect. An abolition of the endothelial NO, for example by injury of the blood vessel endothelium, leads to high blood pressure in the entire organism and is probably involved in the development of arteriosclerosis. In addition, it is important for the function of NO that its biological half-life is shorter than one second. Therewith, NO can only reach the cells in the immediate neighborhood of the location of formation, i.e. the effect of NO is locally limited.

At least three different NOS isozymes belong to the family of NOS: the endothelial enzyme (eNOS), the brain enzyme (bNOS) and the inducible NOS (iNOS). All three isozymes are isolated by now, their primary structure, i.e. amino acid sequence, solved and the coding gene segments characterized. The essential difference between these NOS lies in their molecular weight and above all in the regulation of the expression and the enzymatic activity. Thus, eNOS and bNOS are regulated through their activity and i-NOS chiefly through expression.

For the characterization of the NOS enzymes the following is illustrated:

eNOS: this enzyme has a molecular weight of 133 kDa, has a binding site for calmodulin which is dependent on free $Ca^{++}$ concentration and is present to more than 90% as membrane bound.

bNOS: the brain enzyme is a homodimer with a molecular weight of 160 kDa per subunit which is present at less than 10% as membrane bound. As with the eNOS, the calmodulin binding is dependent on free $Ca^{++}$, i.e. both enzymes are only active when the intracellular $Ca^{++}$ concentration is increased, for example as a result of a receptor mediated $Ca^{++}$ influx.

iNOS: the inducible NOS is also a homodimer with a molecular weight of 130 kDa per subunit. The essential difference to the other isozymes is that the activity of iNOS is independent from calmodulin and therewith independent from cellular calcium. Because the turnover rate for L-arginine for iNOS is approximately 10–100 times higher than by eNOS and bNOS, INOS is also referred to as "high output" NOS. Under basal conditions, iNOS can not normally be detected; it is however strongly expressed after immunological activation through inflammation mediators and endotoxins.

OBJECTS OF THE INVENTION

Object of the present invention is to make an expression vector available which is suitable for gene therapeutic treatment of vascular disorders, especially high blood pressure or arteriosclerosis, stenosis or restenosis.

SUMMARY OF THE INVENTION

The above object is solved by a DNA expression vector that comprises a DNA sequence which codes for a protein which expresses the biological activity of nitrogen monoxide synthase and comprises eukaryotic regulation elements, wherein the blood vessels transformed or infected with this DNA expression vector express recombinant nitrogen monoxide synthase in a therapeutically acceptable amount for the inhibition of stenosis or restenosis of said blood vessels and/or for the inhibition of the proliferation of the smooth vessel musculature.

The above expression vector finds use according to the invention in a method for the treatment of vascular disorders, particularly high blood pressure, arteriosclerosis or stenosis, and especially for restenosis of the coronary vessels after percutaneous, transluminal coronary angioplasty.

Furthermore, a pharmaceutical composition is made available.

The inventors have surprisingly found th at the expression of recombinant nitrogen monoxide synthase in blood vessels which were transfected with a DNA expression vector described here leads to a therapeutically relevant inhibition of vessel stenosis and restenosis after percutaneous, transluminal coronary angioplasty.

The invention relates to a DNA sequence, preferably a cDNA sequence, which is obtained from mammals, preferably mice or humans, which codes for iNOS, bNOS or eNOS, preferably iNOS, activity. The iNOS cDNA is preferably employed because it has a higher specific activity which is furthermore Ca independent. The enzyme activity is therefore independent from regulatory influences.

The DNA expression vector can comprise a sequence element which allows replication in bacteria, a sequence element which allows the replication of said vector in eukaryotic cells, preferably the SV40 replication sequence element, a polyadeylation signal and one or more introns.

The regulation element can comprise the promoter and/or the enhancer region from eukaryotic viruses, preferably from Cytomegalovirus or Adenovirus, and more preferably the promoter-enhancer of the Cytomegalovirus immediate early polypeptide gene.

Additionally, the present invention relates to the treatment and prevention of vascular disorders in humans such as high blood pressure and arteriosclerosis as well as stenosis or restenosis of the blood vessels. The invention particularly relates to a method for the treatment and prevention of restenosis of the coronary vessels after percutaneous, transluminal coronary angioplasty (PTCA), whereby the blood vessels are brought into contact, transfected, or infected with the DNA expression vector described above.

The transfection or infection of the blood vessels with a DNA expression vector can occur by every standard method known in the art and is not limited to the transfection techniques described here.

Furthermore, the invention relates to a pharmaceutical composition which comprise this DNA expression vector for the treatment or prevention of the above mentioned vascular disorders. The pharmaceutical composition can comprise a pharmaceutically acceptable carrier, a stabilizing agent or buffer in addition to the DNA expression vector. The following Figures serve to illustrate the invention.

BRIEF DESCRIPTION OF THE FIGURES

FIG. 1 Nucleotide and amino acid sequence of the inducible NO synthase of mouse (Mus musculus/mammalia deduced from the cloned cDNA, Genbank Accession No.: M92649);

FIG. 2 Nucleotide and amino acid sequence of the neuronal NO synthase of human (Homo sapiens/mammalia deduced from the cloned CDNA, Genbank Accession No.: L02881);

FIG. 3 Nucleotide and amino acid sequence of the endothelial NO synthase of bovine (Bos taurus/mammalia deduced from the cloned cDNA, Genbank Accession No.: M95674);

DETAILED DESCRIPTION OF THE INVENTION

The following Examples should more closely illustrate the invention without limiting it to them.

EXAMPLE 1

I. Elements of an Expression Vector

The expression plasmid pSCMV-iNOS was cloned based on the plasmid pS065 (Promega Biotech). It contains the following functional elements:

promoter/enhancer of the human Cytomegalovirus immediate early polypeptide (Pos. 216-809/ Genbank Accession No.: K03104)

cDNA of the inducible NO synthase of the mouse (Pos. 127-4110/ Genbank Accession No.: M92649)

genomic sequences of β-globin gene of rabbit (Pos. 905-2080) which contains intron 2, exon 3 and the polyadenylation signal (Pos. 905-1827 are stored under Genbank Accession No.: J00659)

the origin of replication of SV40 virus (Pos. 130 [SV40 early map] or Pos. 5176-130 of the circular SV40 map Genbank Accession No.: V01380).

II. Production of an Expression Vector

Figure 4A:
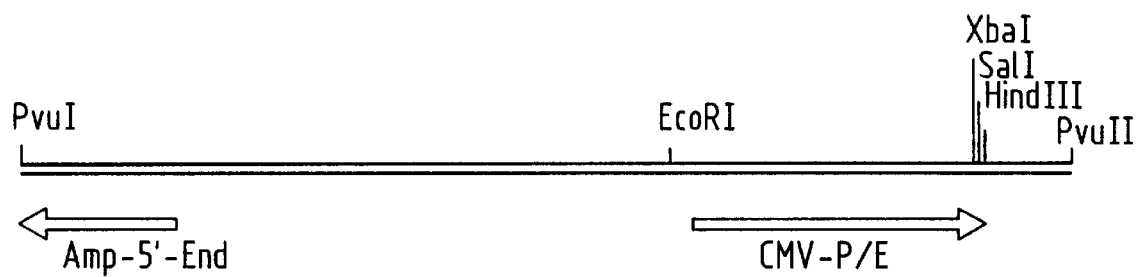
FIG. 4a the 2.17 Kb CMV promoter containing PvuI-PvuII fragment which was isolated from the plasmid pSP65h-CMV for the further construction of the plasmid pSCMV.

The CMV promoter/enhancer was present as a DNA fragment inserted in the SmaI site of the plasmids pSP65 with blunt ends (pSP65h-CMV1). The PvuI-PvuII fragment was isolated from this plasmid which carries the CMV promoter (FIG. 4a).

Figure 4B:
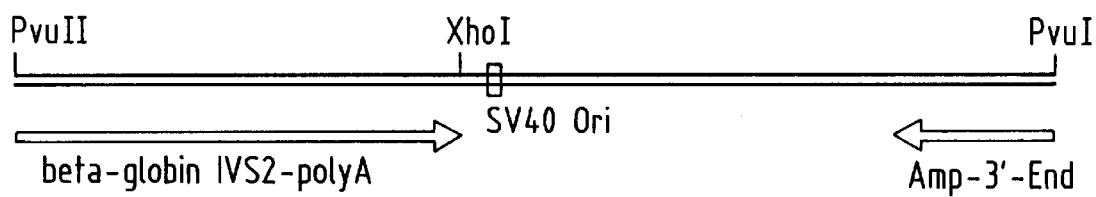
FIG. 4b the PvuI-PvuII fragment containing the 2.80 Kb 3' region of the β-globin gene and the SV40 origin of replication which was isolated from the plasmid pSCT GAL X-556 for the further construction of the plasmid pCMV.
Figure 4C:
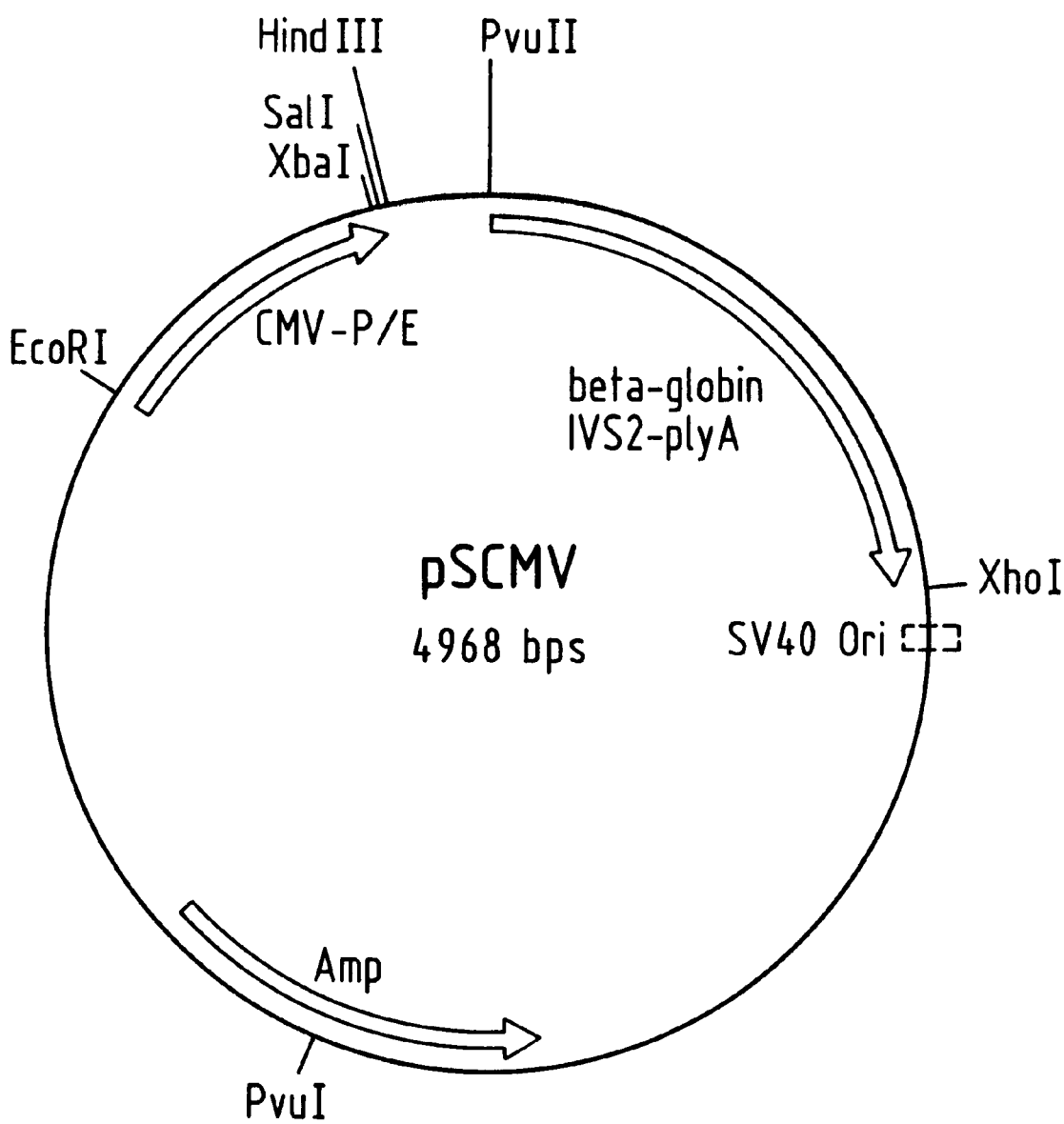
FIG. 4c the plasmid pSCMV.

A PvuI-PvuII fragment which carries the 3' region of the β-globin gene and the SV40 origin of replication (FIG. 4b) was isolated from the plasmid pSCT GAL.X-556 (see FIG. 4b). This fragment was ligated with the PvuI-PvuII fragment from pSP65h-CMV1. From the resulting plasmid (pSCMV, FIG. 4c), the following alterations were performed:

deletion of the vector sequences between HindIII and PvuII with simultaneous insertion of a ClaI linker. Thereby, the starting cleavage sites PvuII and HindIII were lost.

conversion of the XhoI cleavage site into a PvuI cleavage site.

The vector obtained is designated as pSCMV2.

Figure 4D:
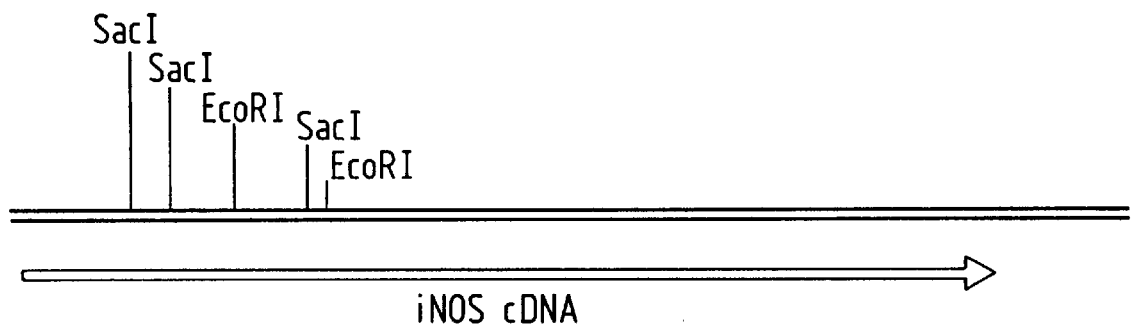
FIG. 4d the 3.97 Kb iNOS containing HindIII-XhoI fragment according to FIG. 1.
Figure 4E:
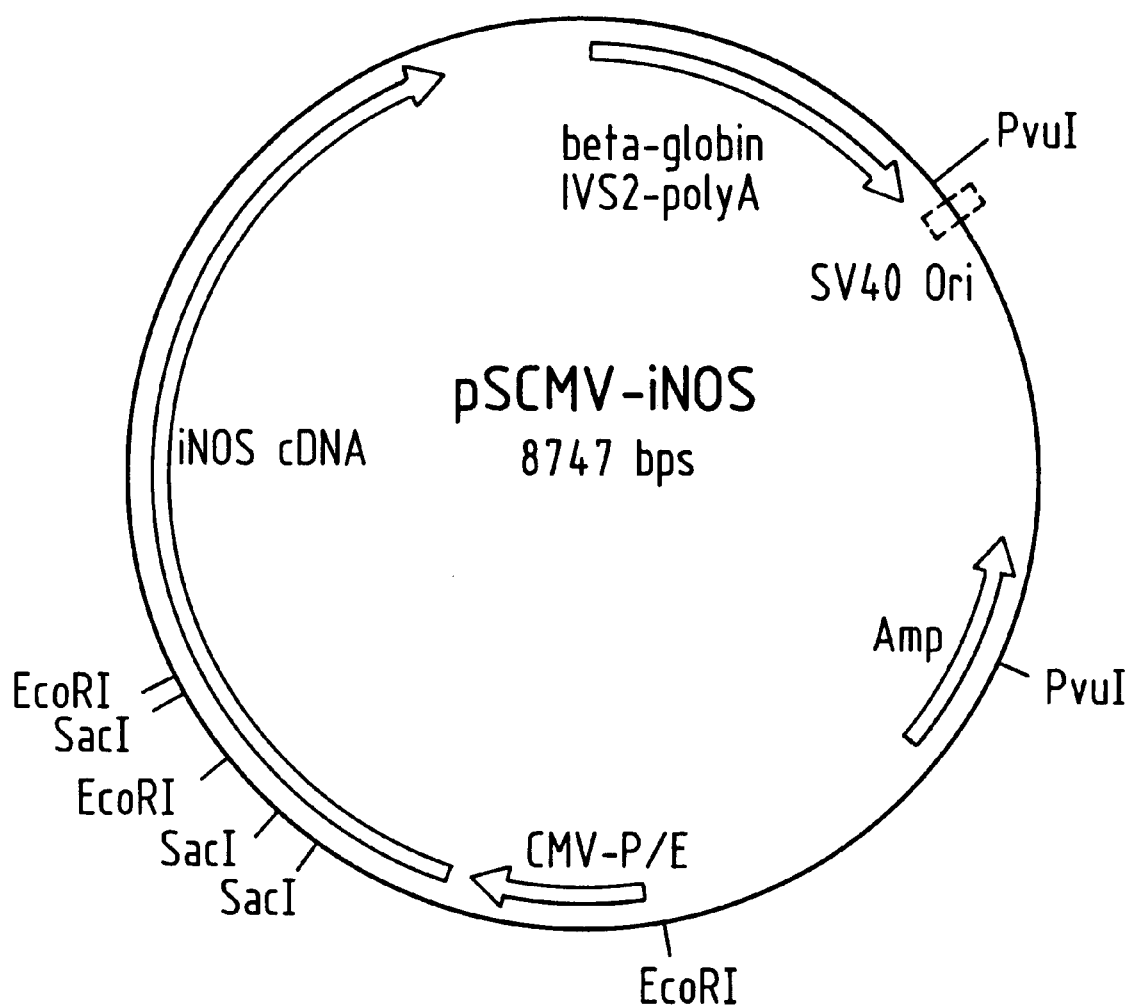
FIG. 4e the plasmid pSCMV-iNOS.

The iNOS cDNA was cloned as a HindIII-XhoI fragment in the XbaI-SalI digested vector pSCMV2 (FIG. 4d). Additionally, the 5' overhanging ends were converted to blunt ends by filling in after the XbaI digestion. At the 3' end, the cDNA was fused with the intron and the polyadenylation signal of the β-globin gene from chicken. The functionality of the construct was verified by transfection of SOS cells and subsequently by detection of the enzyme activity. The resulting plasmid pSCMV-iNOS (FIG. 4e) was employed for the transfection experiments. The CMV promoter imparts a constitutive expression of the iNOS gene. The activity of the enzyme made is Ca independent.

III. Production of DNA Liposome Complexes

The cultivation of Sendi virus occurred in the chorionallantis fluid of fertilized chicken eggs (d10–d12 of the embryonic development) according to standard methods (Nakanishi M., Uchida T., Sugawa H., Ishiura M., Okada Y., Exp. Cell Res. 159, 399–409).

Phosphatidylcholine, phosphatidylserine and cholesterol were dissolved in tetrahydrofuran, mixed in a molar ratio of 4.8:1:2 and evaporated under nitrogen. 10 mg of the dried lipids were suspended by vortexing in 200 μl pSCMV-iNOS [dissolved in BSS (140 mM NaCl, 5.4 mM KCl and 10 mM Tris-HCl, pH 7.69)] (conc. 1 μg/μl). The liposomes obtained were incubated with 4 ml Sendi virus (Z strain) (16000 hemagglutination units (HAU)/ml) for 3 h at 37° C. under light shaking and subsequently sonicated for 20" in the ultrasonic bath. The viruses were inactivated before use with LTV light (11 J/m$^2$×s). The suspension obtained was loaded on two saccharose gradients (1 ml 60%, 1 ml 40%, 8 ml 30% saccharose in BSS) and centrifuged for 3 h at 30,000 rpm in the SW40 rotor (Beckman Instruments) at 4° C. The top 2 ml were collected and employed for the transfection experiments.

IV. Transfection Protocol

To investigate the effects of a local over-expression of iNOS on the proliferation of the smooth vessel musculature after endothelial injury in vivo, the established restenosis rat model of Clowes A W, Reidy M A and Clowes M M (Lab. Invest. 49, 327–333, 1983) was used. In the neck region, the common carotid artery was prepared as well as the rostral lying bifurcation at which the common carotid artery branches into the external carotid artery and internal carotid artery. The external carotid artery was permanently ligated approximately 1 cm rostral from the bifurcation; the internal carotid artery was temporarily ligated by a vessel clamp. The external carotid artery was opened by a cut approximately 0.5 cm rostral from the bifurcation. A Fogarty 2F embolectomy catheter was lead into the common carotid artery through this opening and the endothelium of the common carotid artery was removed by three passages of the dilated catheter.

For the "therapy group", the following method was used. The denuded vessel was closed with a vessel clamp 1.5 to 2 cm caudal from the bifurcation after the removal of the catheter. A polyethylene catheter was integrated in the vessel from the opening in the external carotid artery. Through this catheter 50–100 μl of a solution with DNA liposome complexes were injected within 15–20 min. into the isolated section of the common carotid artery. Care was taken that the vessel section stood under pressure from the liposome solution during the transfection. After removal of the transfection catheter, the external carotid artery was permanently ligated caudal to the vessel incision, and subsequently, the blood flow over the common carotid artery and internal carotid artery was re-established by removal of the vessel clamps.

V. Morphological Analysis of the Vessels

At various time points after the transfection of the common carotid artery (to 21d), rats were examined with respect to the morphological changes in the vessels. The vessels were fixed by per-fusion with 3% paraformaldehyde in PBS (140 mM NaCl, 10 mM Na phosphate, pH 7.5) and sectioned. The degree of the proliferation was compared with control treated vessels. A reduction of the stenosis formation by up to 60% in the treated animals was demonstrated. This study shows for the first time that in this animal model the local over-expression of a gene results in a therapeutically relevant inhibition of vessel stenosis and demonstrates the special roll of NO for the inhibition of the proliferation of smooth vessel musculature.

What is claimed is:

1. A pharmaceutical composition comprising as an active ingredient a pharmaceutical agent comprising a DNA sequence that codes for a protein which possesses the biological activity of inducible nitrogen monoxide synthase (iNOS) and eukaryotic regulation elements, wherein said eukaryotic regulation elements result in the expression of said DNA sequence in eukaryotic cells, and a pharmaceutically acceptable carrier.

2. The pharmaceutical composition according to claim 1, wherein the DNA sequence that codes for a protein which possesses the biological activity of inducible nitrogen monoxide synthase (iNOS) is a cDNA sequence.

3. The pharmaceutical composition according to claim 1 or 2, wherein the DNA or cDNA sequence is derived from mammals.

4. The pharmaceutical composition according to claim 3, wherein the DNA or CDNA sequence constitutes a human DNA or cDNA sequence.

5. The pharmaceutical composition according to claim 1, wherein said eukaryotic regulation elements are derived from the Cytomegalovirus (CMV) promoter and/or enhancer of the early gene.

6. The pharmaceutical composition according to claim 1, wherein said eukaryotic regulation elements are derived from an eukaryotic virus.

7. The pharmaceutical composition according to claim 1, wherein said DNA expression vector represents pSCMV-iNOS according to FIG. 4e.

8. The pharmaceutical composition according to claim 1, wherein said eukaryotic regulation elements are derived from an Adenovirus promoter and/or enhancer element.

9. A pharmaceutical composition comprising as an active ingredient a pharmaceutical agent comprising the plasmid pSCMV-iNOS according to FIG. 4e which contains a DNA sequence that codes for a protein which possesses the biological activity of inducible nitrogen monoxide synthase (INOS) and eukaryotic regulation elements, wherein said eukaryotic regulations elements result in the expression of said DNA sequence in eukaryotic cells, and a pharmaceutically acceptable carrier.

* * * * *

UNITED STATES PATENT AND TRADEMARK OFFICE
CERTIFICATE OF CORRECTION

PATENT NO. : 6,146,887
DATED : November 14, 2000
INVENTOR(S) : Schrader, et al

It is certified that error appears in the above-identified patent and that said Letters Patent is hereby corrected as shown below:

<u>Title page</u>,
Item [73] assignee: Ju<u>e</u>rgen Schrader, Du<u>e</u>sseldorf, Germany <u>Claim 4</u>,
Line 2, change "CDNA" to -- cDNA --

<u>Claim 9</u>,
Line 6, please change "(INOS)" to -- (iNOS) --.

Signed and Sealed this

Twenty-eighth Day of August, 2001

Attest:

NICHOLAS P. GODICI
*Attesting Officer*     *Acting Director of the United States Patent and Trademark Office*

SEQUENCE LISTING

<160> NUMBER OF SEQ ID NOS: 6

<210> SEQ ID NO 1
<211> LENGTH: 4110
<212> TYPE: DNA
<213> ORGANISM: Cytomegalovirus

<400> SEQUENCE: 1

```
gagactctgg ccccacggga cacagtgtca ctggtttgaa acttctcagc caccttggtg      60
aagggactga gctgttagag acacttctga ggctcctcac gcttgggtct tgttcactcc     120
acggagtagc ctagtcaact gcaagagaac ggagaacgtt ggatttggag cagaagtgca     180
aagtctcaga catggcttgc ccctggaagt ttctcttcaa agtcaaatcc taccaaagtg     240
acctgaaaga ggaaaaggac attaacaaca acgtgaagaa aaccccttgt gctgttctca     300
gcccaacaat acaagatgac cctaagagtc accaaaatgg ctccccgcag ctcctcactg     360
ggacagcaca gaatgttcca gaatccctgg acaagctgca tgtgacatcg acccgtccac     420
agtatgtgag gatcaaaaac tggggcagtg gagagatttt gcatgacact cttcaccaca     480
aggccacatc ggatttcact tgcaagtcca agtcttgctt ggggtccatc atgaacccca     540
agagtttgac cagaggaccc agagacaagc ctaccctct ggaggagctc ctgcctcatg      600
ccattgagtt catcaaccag tattatggct cctttaaaga ggcaaaaata gaggaacatc     660
```

-continued

```
tggccaggct ggaagctgta acaaaggaaa tagaaacaac aggaacctac cagctcactc      720
tggatgagct catctttgcc accaagatgg cctggaggaa tgcccctcgc tgcatcggca      780
ggatccagtg gtccaacctg caggtctttg acgctcggaa ctgtagcaca gcacaggaaa      840
tgtttcagca catctgcaga cacatacttt atgccaccaa caatggcaac atcaggtcgg      900
ccatcactgt gttcccccag cggagtgacg gcaaacatga cttcaggctc tggaattcac      960
agctcatccg gtacgctggc taccagatgc ccgatggcac catcagaggg gatgctgcca     1020
ccttggagtt cacccagttg tgcatcgacc taggctggaa gccccgctat ggccgctttg     1080
atgtgctgcc tctggtcttg caagctgatg gtcaagatcc agaggtcttt gaaatccctc     1140
ctgatcttgt gttggaggtg accatggagc atcccaagta cgagtggttc caggagctcg     1200
ggttgaagtg gtatgcactg cctgccgtgg ccaacatgct actggaggtg ggtggcctcg     1260
aattcccagc ctgccccttc aatggttggt acatgggcac cgagattgga gttcgagact     1320
tctgtgacac acagcgctac aacatcctgg aggaagtggg ccgaaggatg ggcctggaga     1380
cccacacact ggcctccctc tggaaagacc gggctgtcac ggagatcaat gtggctgtgc     1440
tccatagttt ccagaagcag aatgtgacca tcatggacca ccacacagcc tcagagtcct     1500
tcatgaagca catgcagaat gagtaccggg cccgtggagg ctgcccggca gactggatt      1560 ggctggtccc tccagtgtct gggagcatca cccctgtgtt ccaccaggag atgttgaact     1620
atgtcctatc tccattctac tactaccaga tcgagccctg gaagacccac atctggcaga     1680
atgagaagct gaggcccagg aggagagaga tccgatttag agtcttggtg aaagtggtgt     1740
tctttgcttc catgctaatg cgaaaggtca tggcttcacg ggtcagagcc acagtcctct     1800
ttgctactga gacagggaag tctgaagcac tagccaggga cctggccacc ttgttcagct     1860
acgccttcaa caccaaggtt gtctgcatgg accagtataa ggcaagcacc ttggaagagg     1920
agcaactact gctggtggtg acaagcacat ttgggaatgg agactgtccc agcaatgggc     1980
agactctgaa gaaatctctg ttcatgctta gagaactcaa ccacaccttc aggtatgctg     2040
tgtttggcct tggctccagc atgtaccctc agttctgcgc ctttgctcat gacatcgacc     2100
agaagctgtc ccacctggga gcctctcagc ttgccccaac aggagaaggg gacgaactca     2160
gtgggcagga ggatgccttc cgcagctggg ctgtacaaac cttccgggca gcctgtgaga     2220
cctttgatgt ccgaagcaaa catcacattc agatcccgaa acgcttcact tccaatgcaa     2280
catgggagcc acagcaatat aggctcatcc agagcccgga gcctttagac ctcaacagag     2340
ccctcagcag catccatgca agaacgtgt ttaccatgag gctgaaatcc agcagaatc      2400 tgcagagtga aaagtccagc cgcaccaccc tcctcgttca gctcaccttc gagggcagcc     2460
gagggcccag ctacctgcct ggggaacacc tggggatctt cccaggcaac cagaccgccc     2520
tggtgcagga atcttggag cgagttgtgg attgtcctac accaccaa actgtgtgcc      2580 tggaggttct ggatgagagc ggcagctact gggtcaaaga caagaggctg cccccctgct     2640
cactcagcca agccctcacc tacttcctgg acattacgac ccctcccacc cagctgcagc     2700
tccacaagct ggctcgcttt gccacggacg agacggatag cagagattg gaggccttgt      2760 gtcagccctc agagtacaat gactggaagt tcagcaacaa ccccacgttc ctggaggtgc     2820
ttgaagagtt ccccttcctt catgtgcccg ctgccttcct gctgtcgcag ctccctatct     2880
tgaagccccg ctactactcc atcagctcct cccaggacca caccccctcg gaggttcacc     2940
tcactgtggc cgtggtcacc taccgcaccc gagatggtca gggtcccctg caccatggtg     3000
```

-continued

```
tctgcagcac ttggatcagg aacctgaagc cccaggaccc agtgccctgc tttgtgcgaa   3060
gtgtcagtgg cttccagctc cctgaggacc cctcccagcc ttgcatcctc attgggcctg   3120
gtacgggcat tgctcccttc cgaagtttct ggcagcagcg gctccatgac tcccagcaca   3180
aagggctcaa aggaggccgc atgagcttgg tgtttgggtg ccggcacccg gaggaggacc   3240
acctctatca ggaagaaatg caggagatgg tccgcaagag agtgctgttc caggtgcaca   3300
caggctactc ccggctgccc ggcaaaccca aggtctacgt tcaggacatc gtgcaaaagc   3360
agctggccaa tgaggtactc agcgtgctcc acggggagca gggccacctc tacatttgcg   3420
gagatgtgcg catggctcgg gatgtggcta ccacattgaa gaagctggtg gccaccaagc   3480
tgaacttgag cgaggagcag gtggaagact atttcttcca gctcaagagc cagaaacgtt   3540
atcatgaaga tatcttcggt gcagtctttt cctatggggc aaaaaagggc agcgccttgg   3600
aggagcccaa agccacgagg ctctgacagc ccagagttcc agcttctggc actgagtaaa   3660
gataatggtg aggggcttgg ggagacagcg aaatgcaatc ccccccaagc ccctcatgtc   3720 attccccccct cctccaccct accaagtagt attgtattat tgtggactac taaatctctc   3780
tcctctcctc cctcccctct ctcccttttcc tcccttcttc tccactcccc agctccctcc   3840
ttctccttct cctcctttgc ctctcactct tccttggagc tgagagcaga gaaaaactca   3900
acctcctgac tgaagcactt tgggtcacca ccaggaggca ccatgccgcc gctctaatac   3960
ttagctgcac tatgtacaga tatttatact tcatatttaa gaaaacagat acttttgtct   4020
actcccaatg atggcttggg cctttcctgt ataattcctt gatgaaaaat atttatataa   4080
aatacatttt attttaatca aaaaaaaaaa                                    4110
```

```
<210> SEQ ID NO 2
<211> LENGTH: 1144
<212> TYPE: PRT
<213> ORGANISM: Cytomegalovirus

<400> SEQUENCE: 2

Met Ala Cys Pro Trp Lys Phe Leu Phe Lys Val Lys Ser Tyr Gln Ser
 1               5                  10                  15

Asp Leu Lys Glu Glu Lys Asp Ile Asn Asn Asn Val Lys Lys Thr Pro
                20                  25                  30

Cys Ala Val Leu Ser Pro Thr Ile Gln Asp Asp Pro Lys Ser His Gln
            35                  40                  45

Asn Gly Ser Pro Gln Leu Leu Thr Gly Thr Ala Gln Asn Val Pro Glu
        50                  55                  60

Ser Leu Asp Lys Leu His Val Thr Ser Thr Arg Pro Gln Tyr Val Arg
65                  70                  75                  80

Ile Lys Asn Trp Gly Ser Gly Glu Ile Leu His Asp Thr Leu His His
                85                  90                  95

Lys Ala Thr Ser Asp Phe Thr Cys Lys Ser Lys Ser Cys Leu Gly Ser
            100                 105                 110

Ile Met Asn Pro Lys Ser Leu Thr Arg Gly Pro Arg Asp Lys Pro Thr
        115                 120                 125

Pro Leu Glu Glu Leu Leu Pro His Ala Ile Glu Phe Ile Asn Gln Tyr
    130                 135                 140

Tyr Gly Ser Phe Lys Glu Ala Lys Ile Glu Glu His Leu Ala Arg Leu
145                 150                 155                 160

Glu Ala Val Thr Lys Glu Ile Gly Thr Thr Gly Thr Tyr Gln Leu Thr
                165                 170                 175
```

-continued

```
Leu Asp Glu Leu Ile Phe Ala Thr Lys Met Ala Trp Arg Asn Ala Pro
            180                 185                 190

Arg Cys Ile Gly Arg Ile Gln Trp Ser Asn Leu Gln Val Phe Asp Ala
        195                 200                 205

Arg Asn Cys Ser Thr Ala Gln Glu Met Phe Gln His Ile Cys Arg His
        210                 215                 220

Ile Leu Tyr Ala Thr Asn Asn Gly Asn Ile Arg Ser Ala Ile Thr Val
225                 230                 235                 240

Phe Pro Gln Arg Ser Asp Gly Lys His Asp Phe Arg Leu Trp Asn Ser
                245                 250                 255

Gln Leu Ile Arg Tyr Ala Gly Tyr Gln Met Pro Asp Gly Thr Ile Arg
            260                 265                 270

Gly Asp Ala Ala Thr Leu Glu Phe Thr Gln Leu Cys Ile Asp Leu Gly
        275                 280                 285

Trp Lys Pro Arg Tyr Gly Arg Phe Asp Val Leu Pro Leu Val Leu Gln
        290                 295                 300

Ala Asp Gly Gln Asp Pro Glu Val Phe Glu Ile Pro Pro Asp Leu Val
305                 310                 315                 320

Leu Glu Val Thr Met Glu His Pro Lys Tyr Glu Trp Phe Gln Glu Leu
                325                 330                 335

Gly Leu Lys Trp Tyr Ala Leu Pro Ala Val Ala Asn Met Leu Leu Glu
            340                 345                 350

Val Gly Gly Leu Glu Phe Pro Ala Cys Pro Phe Asn Gly Trp Tyr Met
        355                 360                 365

Gly Thr Glu Ile Gly Val Arg Asp Phe Cys Asp Thr Gln Arg Tyr Asn
        370                 375                 380

Ile Leu Glu Glu Val Gly Arg Arg Met Gly Leu Glu Thr His Thr Leu
385                 390                 395                 400

Ala Ser Leu Trp Lys Asp Arg Ala Val Thr Glu Ile Asn Val Ala Val
                405                 410                 415

Leu His Ser Phe Gln Lys Gln Asn Val Thr Ile Met Asp His His Thr
            420                 425                 430

Ala Ser Glu Ser Phe Met Lys His Met Gln Asn Glu Tyr Arg Ala Arg
        435                 440                 445

Gly Gly Cys Pro Ala Asp Trp Ile Trp Leu Val Pro Pro Val Ser Gly
        450                 455                 460

Ser Ile Thr Pro Val Phe His Gln Glu Met Leu Asn Tyr Val Leu Ser
465                 470                 475                 480

Pro Phe Tyr Tyr Tyr Gln Ile Glu Pro Trp Lys Thr His Ile Trp Gln
                485                 490                 495

Asn Glu Lys Leu Arg Pro Arg Arg Glu Ile Arg Phe Arg Val Leu
            500                 505                 510

Val Lys Val Val Phe Phe Ala Ser Met Leu Met Arg Lys Val Met Ala
            515                 520                 525

Ser Arg Val Arg Ala Thr Val Leu Phe Ala Thr Glu Thr Gly Lys Ser
        530                 535                 540

Glu Ala Leu Ala Arg Asp Leu Ala Thr Leu Phe Ser Tyr Ala Phe Asn
545                 550                 555                 560

Thr Lys Val Val Cys Met Asp Gln Tyr Lys Ala Ser Thr Leu Glu Glu
                565                 570                 575

Glu Gln Leu Leu Leu Val Val Ser Thr Phe Gly Asn Gly Asp Cys
            580                 585                 590

Pro Ser Asn Gly Gln Thr Leu Lys Lys Ser Leu Phe Met Leu Arg Glu
```

```
                 595                 600                 605
Leu Asn His Thr Phe Arg Tyr Ala Val Phe Gly Leu Gly Ser Ser Met
        610                 615                 620
Tyr Pro Gln Phe Cys Ala Phe Ala His Asp Ile Asp Gln Lys Leu Ser
625                 630                 635                 640
His Leu Gly Ala Ser Gln Leu Ala Pro Thr Gly Glu Gly Asp Glu Leu
                645                 650                 655
Ser Gly Gln Glu Asp Ala Phe Arg Ser Trp Ala Val Gln Thr Phe Arg
                660                 665                 670
Ala Ala Cys Glu Thr Phe Asp Val Arg Ser Lys His Ile Gln Ile
            675                 680                 685
Pro Lys Arg Phe Thr Ser Asn Ala Thr Trp Glu Pro Gln Gln Tyr Arg
        690                 695                 700
Leu Ile Gln Ser Pro Glu Pro Leu Asp Leu Asn Arg Ala Leu Ser Ser
705                 710                 715                 720
Ile His Ala Lys Asn Val Phe Thr Met Arg Leu Lys Ser Gln Gln Asn
                725                 730                 735
Leu Gln Ser Glu Lys Ser Ser Arg Thr Thr Leu Leu Val Gln Leu Thr
                740                 745                 750
Phe Glu Gly Ser Arg Gly Pro Ser Tyr Leu Pro Gly Glu His Leu Gly
            755                 760                 765
Ile Phe Pro Gly Asn Gln Thr Ala Leu Val Gln Gly Ile Leu Glu Arg
770                 775                 780
Val Val Asp Cys Pro Thr Pro His Gln Thr Val Cys Leu Glu Val Leu
785                 790                 795                 800
Asp Glu Ser Gly Ser Tyr Trp Val Lys Asp Lys Arg Leu Pro Pro Cys
                805                 810                 815
Ser Leu Ser Gln Ala Leu Thr Tyr Phe Leu Asp Ile Thr Thr Pro Pro
                820                 825                 830
Thr Gln Leu Gln Leu His Lys Leu Ala Arg Phe Ala Thr Asp Glu Thr
            835                 840                 845
Asp Arg Gln Arg Leu Glu Ala Leu Cys Gln Pro Ser Glu Tyr Asn Asp
        850                 855                 860
Trp Lys Phe Ser Asn Asn Pro Thr Phe Leu Glu Val Leu Glu Glu Phe
865                 870                 875                 880
Pro Ser Leu His Val Pro Ala Ala Phe Leu Leu Ser Gln Leu Pro Ile
                885                 890                 895
Leu Lys Pro Arg Tyr Tyr Ser Ile Ser Ser Ser Gln Asp His Thr Pro
                900                 905                 910
Ser Glu Val His Leu Thr Val Ala Val Val Thr Tyr Arg Thr Arg Asp
            915                 920                 925
Gly Gln Gly Pro Leu His His Gly Val Cys Ser Thr Trp Ile Arg Asn
        930                 935                 940
Leu Lys Pro Gln Asp Pro Val Pro Cys Phe Val Arg Ser Val Ser Gly
945                 950                 955                 960
Phe Gln Leu Pro Glu Asp Pro Ser Gln Pro Cys Ile Leu Ile Gly Pro
                965                 970                 975
Gly Thr Gly Ile Ala Pro Phe Arg Ser Phe Trp Gln Gln Arg Leu His
            980                 985                 990
Asp Ser Gln His Lys Gly Leu Lys Gly Gly Arg Met Ser Leu Val Phe
        995                 1000                1005
Gly Cys Arg His Pro Glu Glu Asp His Leu Tyr Gln Glu Glu Met Gln
    1010                1015                1020
```

```
Glu Met Val Arg Lys Arg Val Leu Phe Gln Val His Thr Gly Tyr Ser
1025                1030                1035                1040

Arg Leu Pro Gly Lys Pro Lys Val Tyr Val Gln Asp Ile Val Gln Lys
            1045                1050                1055

Gln Leu Ala Asn Glu Val Leu Ser Val Leu His Gly Glu Gln Gly His
        1060                1065                1070

Leu Tyr Ile Cys Gly Asp Val Arg Met Ala Arg Asp Val Ala Thr Thr
            1075                1080                1085

Leu Lys Lys Leu Val Ala Thr Lys Leu Asn Leu Ser Glu Glu Gln Val
        1090                1095                1100

Glu Asp Tyr Phe Phe Gln Leu Lys Ser Gln Lys Arg Tyr His Glu Asp
1105                1110                1115                1120

Ile Phe Gly Ala Val Phe Ser Tyr Gly Ala Lys Lys Gly Ser Ala Leu
            1125                1130                1135

Glu Glu Pro Lys Ala Thr Arg Leu
            1140

<210> SEQ ID NO 3
<211> LENGTH: 4780
<212> TYPE: DNA
<213> ORGANISM: Cytomegalovirus

<400> SEQUENCE: 3
gagcggacgg gctcatgatg cctcagatct gatccgcatc taacaggctg caatgaaga      60
tacccagaga atagttcaca tctatcatgc gtcacttcta gacacagcca tcagacgcat   120
ctcctcccct ttctgcctga ccttaggaca cgtcccaccg cctctcttga cgtctgcctg   180
gtcaaccatc acttccttag agaataagga gagaggcgga tgcaggaaat catgccaccg   240
acgggccacc agccatgagt gggtgacgct gagctgacgt caaagacaga gagggctgaa   300
gccttgtcag cacctgtcac cccggctcct gctctccgtg tagcctgaag cctggatcct   360
cctggtgaaa tcatcttggc ctgatagcat tgtgaggtct tcagacagga ccctcggaa    420
gctagttacc atggaggatc acatgttcgg tgttcagcaa atccagccca atgtcatttc   480
tgttcgtctc ttcaagcgca aagttggggg cctgggattt ctggtgaagg agcgggtcag   540
taagccgccc gtgatcatct ctgacctgat tcgtggggggc gccgcagagc agagtggcct   600
catccaggcc ggagacatca ttcttgcggt caacggccgg cccttggtgg acctgagcta   660
tgacagcgcc ctggaggtac tcagaggcat tgcctctgag acccacgtgg tcctcattct   720
gaggggccct gaaggtttca ccacgcacct ggagaccacc tttacaggtg atgggacccc   780
caagaccatc cgggtgacac agcccctggg tcccccccacc aaagccgtgg atctgtccca   840
ccagccaccg gccggcaaag aacagccccct ggcagtggat ggggcctcgg gtcccgggaa   900
tgggcctcag catgcctacg atgatgggca ggaggctggc tcactccccc atgccaacgg   960
ctggccccag gcccccaggc aggaccccgc gaagaaagca accagagtca gcctccaagg  1020
cagaggggag aacaatgaac tgctcaagga gatagagcct gtgctgagcc ttctcaccag  1080
tgggagcaga ggggtcaagg gaggggcacc tgccaaggca gagatgaaag atatgggaat  1140
ccaggtggac agagatttgg acggcaagtc acacaaacct ctgcccctcg gcgtggagaa  1200
cgaccgagtc ttcaatgacc tatggggaa gggcaatgtg cctgtcgtcc tcaacaaccc  1260
atattcagag aaggagcagc ccccacctc aggaaaacag tccccacaa agaatggcag  1320
cccctccaag tgtccacgct tcctcaaggt caagaactgg gagactgagg tggttctcac  1380
```

-continued

```
tgacaccctc caccttaaga gcacattgga aacgggatgc actgagtaca tctgcatggg    1440
ctccatcatg catccttctc agcatgcaag gaggcctgaa gacgtccgca caaaaggaca    1500
gctcttccct ctcgccaaag agtttattga tcaatactat tcatcaatta aaagatttgg    1560
ctccaaagcc cacatggaaa ggctggaaga ggtgaacaaa gagatcgaca ccactagcac    1620
ttaccagctc aaggacacag agctcatcta tggggccaag cacgcctggc ggaatgcctc    1680
gcgctgtgtg ggcaggatcc agtggtccaa gctgcaggta ttcgatgccc gtgactgcac    1740
cacggcccac gggatgttca actacatctg taaccatgtc aagtatgcca ccaacaaagg    1800
gaacctcagg tctgccatca ccatattccc ccagaggaca gacggcaagc acgacttccg    1860
agtctggaac tcccagctca tccgctacgc tggctacaag caccgtgacg gctccaccct    1920
gggggaccca gccaatgtgc agttcacaga gatatgcata cagcagggct ggaaaccgcc    1980
tagaggccgc ttcgatgtcc tgccgctcct gcttcaggcc aacggcaatg accctgagct    2040
cttccagatt cctccagagc tggtgttgga acttcccatc aggcacccca gtttgagtg    2100 gttcaaggac ctggcgctga gtggtacgg cctccccgcc gtgtccaaca tgctcctaga    2160
gattggcggc ctggagttca gcgcctgtcc cttcagtggc tggtacatgg gcacagagat    2220
tggtgtccgc gactactgtg acaactcccg ctacaatatc ctggaggaag tggccaagaa    2280
gatgaactta gacatgagga gacgtcctc cctgtggaag gaccaggcgc tggtggagat    2340
caatatcgcg gttctctata gcttccagag tgacaaagtg accattgttg accatcactc    2400
cgccaccgag tccttcatta agcacatgga gaatgagtac cgctgccggg ggggctgccc    2460
tgccgactgg gtgtggatcg tgcccccccat gtccggaagc atcacccctg tgttccacca    2520
ggagatgctc aactaccggc tcacccctc cttcgaatac cagcctgatc cctggaacac    2580
gcatgtctgg aaaggcacca acgggacccc cacaaagcgg cgagccatcg gcttcaagaa    2640
gctagcagaa gctgtcaagt tctcggccaa gctgatgggg caggctatgg ccaagagggt    2700
gaaagcgacc atcctctatg ccacagagac aggcaaatcg caagcttatg ccaagacctt    2760
gtgtgagatc ttcaaacacg cctttgatgc caaggtgatg tccatggaag aatatgacat    2820
tgtgcacctg gaacatgaaa ctctggtcct tgtggtcacc agcacctttg gcaatggaga    2880
tccccctgag aatggggaga aattcggctg tgctttgatg gaaatgaggc accccaactc    2940
tgtgcaggaa gaaaggaaga gctacaaggt ccgattcaac agcgtctcct cctactctga    3000
ctcccaaaaa tcatcaggcg atgggcccga cctcagagac aactttgaga gtgctggacc    3060
cctggccaat gtgaggttct cagttttgg cctcggctca cgagcatacc ctcacttttg    3120
cgccttcgga cacgctgtgg acaccctcct ggaagaactg ggaggggaga ggatcctgaa    3180
gatgagggaa ggggatgagc tctgtgggca ggaagaggct tcaggacct gggccaagaa    3240 ggtcttcaag gcagcctgtg atgtcttctg tgtgggagat gatgtcaaca ttgaaaaggc    3300
caacaattcc ctcatcagca atgatcgcag ctggaagaga aacaagttcc gcctcacctt    3360
tgtggccgaa gctccagaac tcacacaagg tctatccaat gtccacaaaa agcgagtctc    3420
agctgcccgg ctccttagcc gtcaaaacct ccagagccct aaatccagtc ggtcaactat    3480
cttcgtgcgt ctccacacca acgggagcca ggagctgcag taccagcctg ggaccacct    3540 gggtgtcttc cctggcaacc acgaggacct cgtgaatgcc ctgatcgagc ggctggagga    3600
cgcgccgcct gtcaaccaga tggtgaaagt ggaactgctg gaggagcgga acacggcttt    3660
aggtgtcatc agtaactgga cagacgagct ccgcctcccg ccctgcacca tcttccaggc    3720
cttcaagtac tacctggaca tcaccacgcc accaacgcct ctgcagctgc agcagtttgc    3780
```

```
ctccctagct accagcgaga aggagaagca gcgtctgctg gtcctcagca agggtttgca    3840
ggagtacgag gaatggaaat ggggcaagaa ccccaccatc gtggaggtgc tggaggagtt    3900
cccatctatc cagatgccgg ccaccctgct cctgacccag ctgtccctgc tgcagccccg    3960
ctactattcc atcagctcct ccccagacat gtaccctgat gaagtgcacc tcactgtggc    4020
catcgtttcc taccgcactc gagatggaga aggaccaatt caccacggcg tatgctcctc    4080
ctggctcaac cggatacagg ctgacgaact ggtcccctgt ttcgtgagag gagcacccag    4140
cttccacctg ccccggaacc cccaagtccc ctgcatcctc gttggaccag gcaccggcat    4200 tgccccttc cgaagcttct ggcaacagcg gcaatttgat atccaacaca aggaatgaa      4260 cccctgcccc atggtcctgg tcttcgggtg ccggcaatcc aagatagatc atatctacag    4320
ggaagagacc ctgcaggcca agaacaaggg ggtcttcaga gagctgtaca cggcttactc    4380
ccgggagcca gacaaaccaa agaagtacgt gcaggacatc ctgcaggagc agctggcgga    4440
gtctgtgtac cgagccctga aggagcaagg gggccacata tacgtctgtg gggacgtcac    4500
catggctgct gatgtcctca aagccatcca gcgcatcatg acccagcagg gaagctctc    4560 ggcagaggac gccggcgtat tcatcagccg gatgagggat gacaaccgat accatgagga    4620
tatttttgga gtcaccctgc gaacgatcga agtgaccaac cgccttagat ctgagtccat    4680
tgccttcatt gaagagagca aaaaagacac cgatgaggtt ttcagctcct aactggaccc    4740
tcttgcccag ccggctgcaa gtttgtaagc gcgggacaga                           4780

<210> SEQ ID NO 4
<211> LENGTH: 1433
<212> TYPE: PRT
<213> ORGANISM: Cytomegalovirus

<400> SEQUENCE: 4

Met Glu Asp His Met Phe Gly Val Gln Gln Ile Gln Pro Asn Val Ile
  1               5                  10                  15

Ser Val Arg Leu Phe Lys Arg Lys Val Gly Gly Leu Gly Phe Leu Val
                 20                  25                  30

Lys Glu Arg Val Ser Lys Pro Pro Val Ile Ile Ser Asp Leu Ile Arg
             35                  40                  45

Gly Gly Ala Ala Glu Gln Ser Gly Leu Ile Gln Ala Gly Asp Ile Ile
         50                  55                  60

Leu Ala Val Asn Gly Arg Pro Leu Val Asp Leu Ser Tyr Asp Ser Ala
     65                  70                  75                  80

Leu Glu Val Leu Arg Gly Ile Ala Ser Glu Thr His Val Val Leu Ile
                 85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Ala Gly Lys Glu
    130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Trp Pro Gln Ala Pro Arg Gln Asp Pro Ala Lys Lys Ala Thr Arg
            180                 185                 190
```

-continued

```
Val Ser Leu Gln Gly Arg Gly Glu Asn Asn Glu Leu Leu Lys Glu Ile
        195                 200                 205

Glu Pro Val Leu Ser Leu Leu Thr Ser Gly Ser Arg Gly Val Lys Gly
        210                 215                 220

Gly Ala Pro Ala Lys Ala Glu Met Lys Asp Met Gly Ile Gln Val Asp
225                 230                 235                 240

Arg Asp Leu Asp Gly Lys Ser His Lys Pro Leu Pro Leu Gly Val Glu
                245                 250                 255

Asn Asp Arg Val Phe Asn Asp Leu Trp Gly Lys Gly Asn Val Pro Val
            260                 265                 270

Val Leu Asn Asn Pro Tyr Ser Glu Lys Glu Gln Pro Thr Ser Gly
        275                 280                 285

Lys Gln Ser Pro Thr Lys Asn Gly Ser Pro Ser Lys Cys Pro Arg Phe
        290                 295                 300

Leu Lys Val Lys Asn Trp Glu Thr Glu Val Val Leu Thr Asp Thr Leu
305                 310                 315                 320

His Leu Lys Ser Thr Leu Glu Thr Gly Cys Thr Glu Tyr Ile Cys Met
                325                 330                 335

Gly Ser Ile Met His Pro Ser Gln His Ala Arg Arg Pro Glu Asp Val
            340                 345                 350

Arg Thr Lys Gly Gln Leu Phe Pro Leu Ala Lys Glu Phe Ile Asp Gln
        355                 360                 365

Tyr Tyr Ser Ser Ile Lys Arg Phe Gly Ser Lys Ala His Met Glu Arg
        370                 375                 380

Leu Glu Glu Val Asn Lys Glu Ile Asp Thr Thr Ser Thr Tyr Gln Leu
385                 390                 395                 400

Lys Asp Thr Glu Leu Ile Tyr Gly Ala Lys His Ala Trp Arg Asn Ala
                405                 410                 415

Ser Arg Cys Val Gly Arg Ile Gln Trp Ser Lys Leu Gln Val Phe Asp
            420                 425                 430

Ala Arg Asp Cys Thr Thr Ala His Gly Met Phe Asn Tyr Ile Cys Asn
        435                 440                 445

His Val Lys Tyr Ala Thr Asn Lys Gly Asn Leu Arg Ser Ala Ile Thr
        450                 455                 460

Ile Phe Pro Gln Arg Thr Asp Gly Lys His Asp Phe Arg Val Trp Asn
465                 470                 475                 480

Ser Gln Leu Ile Arg Tyr Ala Gly Tyr Lys His Arg Asp Gly Ser Thr
                485                 490                 495

Leu Gly Asp Pro Ala Asn Val Gln Phe Thr Glu Ile Cys Ile Gln Gln
            500                 505                 510

Gly Trp Lys Pro Pro Arg Gly Arg Phe Asp Val Leu Pro Leu Leu Leu
        515                 520                 525

Gln Ala Asn Gly Asn Asp Pro Glu Leu Phe Gln Ile Pro Pro Glu Leu
        530                 535                 540

Val Leu Glu Leu Pro Ile Arg His Pro Lys Phe Glu Trp Phe Lys Asp
545                 550                 555                 560

Leu Ala Leu Lys Trp Tyr Gly Leu Pro Ala Val Ser Asn Met Leu Leu
                565                 570                 575

Glu Ile Gly Gly Leu Glu Phe Ser Ala Cys Pro Phe Ser Gly Trp Tyr
            580                 585                 590

Met Gly Thr Glu Ile Gly Val Arg Asp Tyr Cys Asp Asn Ser Arg Tyr
        595                 600                 605

Asn Ile Leu Glu Glu Val Ala Lys Lys Met Asn Leu Asp Met Arg Lys
```

```
              610                 615                 620
Thr Ser Ser Leu Trp Lys Asp Gln Ala Leu Val Glu Ile Asn Ile Ala
625                 630                 635                 640

Val Leu Tyr Ser Phe Gln Ser Asp Lys Val Thr Ile Val Asp His His
                645                 650                 655

Ser Ala Thr Glu Ser Phe Ile Lys His Met Glu Asn Glu Tyr Arg Cys
            660                 665                 670

Arg Gly Gly Cys Pro Ala Asp Trp Val Trp Ile Val Pro Pro Met Ser
        675                 680                 685

Gly Ser Ile Thr Pro Val Phe His Gln Glu Met Leu Asn Tyr Arg Leu
    690                 695                 700

Thr Pro Ser Phe Glu Tyr Gln Pro Asp Pro Trp Asn Thr His Val Trp
705                 710                 715                 720

Lys Gly Thr Asn Gly Thr Pro Thr Lys Arg Arg Ala Ile Gly Phe Lys
                725                 730                 735

Lys Leu Ala Glu Ala Val Lys Phe Ser Ala Lys Leu Met Gly Gln Ala
                740                 745                 750

Met Ala Lys Arg Val Lys Ala Thr Ile Leu Tyr Ala Thr Glu Thr Gly
            755                 760                 765

Lys Ser Gln Ala Tyr Ala Lys Thr Leu Cys Glu Ile Phe Lys His Ala
        770                 775                 780

Phe Asp Ala Lys Val Met Ser Met Glu Glu Tyr Asp Ile Val His Leu
785                 790                 795                 800

Glu His Glu Thr Leu Val Leu Val Val Thr Ser Thr Phe Gly Asn Gly
                805                 810                 815

Asp Pro Pro Glu Asn Gly Glu Lys Phe Gly Cys Ala Leu Met Glu Met
                820                 825                 830

Arg His Pro Asn Ser Val Gln Glu Arg Lys Ser Tyr Lys Val Arg
            835                 840                 845

Phe Asn Ser Val Ser Ser Tyr Ser Asp Ser Gln Lys Ser Ser Gly Asp
850                 855                 860

Gly Pro Asp Leu Arg Asp Asn Phe Glu Ser Ala Gly Pro Leu Ala Asn
865                 870                 875                 880

Val Arg Phe Ser Val Phe Gly Leu Gly Ser Arg Ala Tyr Pro His Phe
                885                 890                 895

Cys Ala Phe Gly His Ala Val Asp Thr Leu Leu Glu Glu Leu Gly Gly
            900                 905                 910

Glu Arg Ile Leu Lys Met Arg Glu Gly Asp Glu Leu Cys Gly Gln Glu
        915                 920                 925

Glu Ala Phe Arg Thr Trp Ala Lys Lys Val Phe Lys Ala Ala Cys Asp
    930                 935                 940

Val Phe Cys Val Gly Asp Asp Val Asn Ile Glu Lys Ala Asn Asn Ser
945                 950                 955                 960

Leu Ile Ser Asn Asp Arg Ser Trp Lys Arg Asn Lys Phe Arg Leu Thr
                965                 970                 975

Phe Val Ala Glu Ala Pro Glu Leu Thr Gln Gly Leu Ser Asn Val His
                980                 985                 990

Lys Lys Arg Val Ser Ala Ala Arg Leu Leu Ser Arg Gln Asn Leu Gln
            995                 1000                1005

Ser Pro Lys Ser Ser Arg Ser Thr Ile Phe Val Arg Leu His Thr Asn
        1010                1015                1020

Gly Ser Gln Glu Leu Gln Tyr Gln Pro Gly Asp His Leu Gly Val Phe
    1025                1030                1035                1040
```

```
Pro Gly Asn His Glu Asp Leu Val Asn Ala Leu Ile Glu Arg Leu Glu
            1045                1050                1055

Asp Ala Pro Pro Val Asn Gln Met Val Lys Val Glu Leu Leu Glu Glu
            1060                1065                1070

Arg Asn Thr Ala Leu Gly Val Ile Ser Asn Trp Thr Asp Glu Leu Arg
            1075                1080                1085

Leu Pro Pro Cys Thr Ile Phe Gln Ala Phe Lys Tyr Tyr Leu Asp Ile
            1090                1095                1100

Thr Thr Pro Pro Thr Pro Leu Gln Leu Gln Gln Phe Ala Ser Leu Ala
1105                1110                1115                1120

Thr Ser Glu Lys Glu Lys Gln Arg Leu Leu Val Leu Ser Lys Gly Leu
            1125                1130                1135

Gln Glu Tyr Glu Glu Trp Lys Trp Gly Lys Asn Pro Thr Ile Val Glu
            1140                1145                1150

Val Leu Glu Glu Phe Pro Ser Ile Gln Met Pro Ala Thr Leu Leu Leu
            1155                1160                1165

Thr Gln Leu Ser Leu Leu Gln Pro Arg Tyr Tyr Ser Ile Ser Ser Ser
            1170                1175                1180

Pro Asp Met Tyr Pro Asp Glu Val His Leu Thr Val Ala Ile Val Ser
1185                1190                1195                1200

Tyr Arg Thr Arg Asp Gly Glu Gly Pro Ile His His Gly Val Cys Ser
            1205                1210                1215

Ser Trp Leu Asn Arg Ile Gln Ala Asp Glu Leu Val Pro Cys Phe Val
            1220                1225                1230

Arg Gly Ala Pro Ser Phe His Leu Pro Arg Asn Pro Gln Val Pro Cys
            1235                1240                1245

Ile Leu Val Gly Pro Gly Thr Gly Ile Ala Pro Phe Arg Ser Phe Trp
            1250                1255                1260

Gln Gln Arg Gln Phe Asp Ile Gln His Lys Gly Met Asn Pro Cys Pro
1265                1270                1275                1280

Met Val Leu Val Phe Gly Cys Arg Gln Ser Lys Ile Asp His Ile Tyr
            1285                1290                1295

Arg Glu Glu Thr Leu Gln Ala Lys Asn Lys Gly Val Phe Arg Glu Leu
            1300                1305                1310

Tyr Thr Ala Tyr Ser Arg Glu Pro Asp Lys Pro Lys Lys Tyr Val Gln
            1315                1320                1325

Asp Ile Leu Gln Glu Gln Leu Ala Glu Ser Val Tyr Arg Ala Leu Lys
            1330                1335                1340

Glu Gln Gly Gly His Ile Tyr Val Cys Gly Asp Val Thr Met Ala Ala
1345                1350                1355                1360

Asp Val Leu Lys Ala Ile Gln Arg Ile Met Thr Gln Gln Gly Lys Leu
            1365                1370                1375

Ser Ala Glu Asp Ala Gly Val Phe Ile Ser Arg Met Arg Asp Asp Asn
            1380                1385                1390

Arg Tyr His Glu Asp Ile Phe Gly Val Thr Leu Arg Thr Ile Glu Val
            1395                1400                1405

Thr Asn Arg Leu Arg Ser Glu Ser Ile Ala Phe Ile Glu Glu Ser Lys
            1410                1415                1420

Lys Asp Thr Asp Glu Val Phe Ser Ser
1425                1430

<210> SEQ ID NO 5
<211> LENGTH: 4097
```

```
<212> TYPE: DNA
<213> ORGANISM: Cytomegalovirus

<400> SEQUENCE: 5
gaattcggca cgaggagcca cagagcagac ggaggccgcc cgtccggccc cagcgacatg      60
ggcaacttga agagtgtggg ccaggagccc gggccccct gcggcctggg gctggggctg     120
ggcctcgggc tatgcggcaa gcagggccca gcctccccgg cacctgagcc cagccgggcc     180
cccgcacccg ccaccccgca cgcgccagac cacagcccag ctcccaacag ccccacgctg     240
acccggcctc cggaggggcc caagttccct cgcgtgaaga actgggagct ggggagcatc     300
acctacgaca ctctgtgcgc gcagtcccaa caggacgggc cctgcactcc caggcgctgc     360
ctgggctccc tggtgttgcc ccggaaactg cagacccggc cctccccggg acctccaccc     420
gctgagcagc tgctgagcca ggccagggac ttcatcaacc agtactacag ctccatcaag     480
aggagcggct cccaggctca cgaggagcgg cttcaggagg tggaggccga ggtggcatcc     540
acgggcacca tccacctccg agagagtgag ctggtgttcg gggccaagca ggcctggcgc     600
aatgcacccc gctgcgtggg ccgcatccag tgggggaagc tgcaggtgtt tgatgcccgg     660
gactgcagct cagcacagga gatgttcacc tacatctgca accacatcaa gtacgccacc     720
aaccgcggca accttcgctc ggccatcaca gtgttcccgc agcgcgcccc gggccgcgga     780
gacttccgga tctggaacag ccagctggtg cgctacgcag gctacagaca gcaggatggc     840
tctgtgcgtg gggacccagc caacgtggag atcacggagc tctgcatcca gcacggctgg     900
acccccggaa acggccgctt cgacgtgctg ccctgctgc tccaggcccc agacgaggct     960
ccagagctct ttgttctgcc ccccgagctg gtccttgaag tgcccctagg agcaccccac    1020
actggagtgg ttcgcggccc tgggctgcga tggtatgccc tcccggccgt gtccaacatg    1080
ctgctggaaa tcggggggtct ggagttctcc gcggcccccct tcagcggctg gtacatgagc    1140
acggagattg gcacgcggaa cctgtgtgac cctcaccgct acaatatcct ggaggatgtg    1200
gccgtctgca tggacctcga cacgcggacc acctcgtccc tgtggaagga caaggcggcc    1260
gtggagatca acctggctgt gctgcacagc tttcagctcg ccaaggtgac catcgtggac    1320
caccacgccg ccacggtgtc cttcatgaag cacctggaca cgagcagaa ggccaggggg    1380 ggctgccccg ccgactgggc ctggatcgtg ccccccatct acggcagcct accgcccgtc    1440
ttccaccagg agatggtcaa ctacatcctg tccctgcct tccgctacca gccagacccc    1500
tggaaaggga gcgcgaccaa gggcgccggc atcaccagga agaagacctt taaggaagtg    1560
gccaacgcgg tgaagatctc tgcctcactc atgggcaccc tgatggccaa gcgagtgaaa    1620
gcaaccatcc tgtacgcctc tgagaccggc cgggcccaga gctacgctca gcagctgggg    1680
aggctcttcc ggaaggcctt cgatccccgg gtcctgtgca tggatgagta tgacgtggtg    1740
tccctggagc acgaggcact ggtgctggtg gtgaccagca cctttgggaa tggcgatccc    1800
ccggagaatg gagagagttt tgcagctgcc ctgatggaga tgtcggggcc ctacaacagc    1860
tccccacggc ggaacagca caagagttac aagatccgct caacagcgt ctcctgctca    1920 gacccgctgg tgtcctcctg gcggcggaag agaaaggagt ccagcaacac agacagcgcg    1980
ggggccctgg ggaccctcag gttctgtgtg ttcggactgg gctcccgggc gtaccccccac    2040 ttctgcgcct tcgcgcgagc ggtggacacc cggctggaag agcttggagg ggagcggctg    2100
ctgcagctgg gccagggcga tgagctctgc ggccaggaag aggccttccg tggttgggca    2160
aaggcggcat tccaggcctc ctgcgagacg ttctgcgttg gggaggaggc caaggctgct    2220
```

-continued

```
gcccaggaca tcttcagccc caaacggagc tggaaacgcc agaggtaccg gctgagcgcc    2280
caggccgagg gcctccagct gctgccaggc ctgatccacg tgcacagacg gaagatgttt    2340
caggccacag tcctctcggt ggaaaatctg caaagcagca agtccacccg ggccaccatc    2400
ctggtgcgcc tggacactgc aggccaggag gggctgcagt accagccggg ggaccacata    2460
ggcatctccg cgcccaaccg gccgggcctg gtggaggcgc tgctgagccg cgtggaggac    2520
ccgccaccgc ccaccgagtc tgtggctgtg agcagctgg agaaaggcag cccaggcggc    2580
cctcctccca gctgggtgcg ggacccacgg ctgcccccgt gcaccgtgcg ccaggctctc    2640
accttcttcc tggacatcac ctccccaccc agccccggc ttctccgact gctcagcacc    2700
ctggccgaag aacccagcga gcagcaggag cttgagaccc tcagtcagga ccccggcgc    2760 tacgaggagt ggaagttggt ccgctgcccc acgctgctgg aggtgctgga gcagttcccg    2820
tccgtggcgc tgcccgcccc gctgctcctc acccagctgc cctgctgca gccccggtac    2880 tactctgtca gctcggcccc caacgcccac cccggagagg tccacctcac agtggccgtg    2940
ctggcgtaca ggacccaaga tgggctgggc cccctacact acggggtctg ctccacatgg    3000
ctgagccagc tcaagactgg agaccccgtg ccctgcttca tcaggggggc tccctccttc    3060
cggctgccgc ctgaccccta cgtgccctgc atcctcgtgg ccctggcac tggcatcgcc    3120 cccttccggg gattttggca ggagaggctg catgacattg agagcaaagg gctgcagccg    3180
caccccatga ccctggtgtt cggctgccgc tgctcccaac tcgaccatct ctaccgcgac    3240
gaggtgcagg acgcccagga gcgcggggtg tttggccgcg tcctcaccgc cttctcccgg    3300
gaacctgaca gccccaagac ctacgtacag gacatcctga gaaccgagct ggctgccgag    3360
gtgcaccgcg tgctgtgcct cgagcggggc cacatgtttg tctgcggcga tgtcactatg    3420
gcaaccagcg tcctgcagac ggtgcagcgc atcttggcga cagagggcga catggagctg    3480
gacgaggcgg cgacgtcat cggcgtgctg cgggatcagc aacgctatca cgaggacatt    3540
ttcggcctca cgctgcgcac ccaggaggtg acaagccgta tacgtaccca gagcttttcc    3600
ctgcaggagc ggcatctgcg gggcgcggtg ccctgggcct cgacccgcc cggcccagac    3660 accccggcc cctgagaccc tcttgcttc ccactgcagt tcccggagag agggggctgtc    3720 attccactat ggctctaccg ctgtcctgtt ggcctttacc gggaccggcc acctctcccct    3780 cccctcccaa ggtgacttcc cagagactgt tggattccct gtactatctc atcctctcat    3840
ctctaggtct gtttccccac cctaagtcca tctggaagac ccctcccagc agcggtattc    3900
cagagcctac agtcagccct ttggtgttta ggtgaatttt agattcccct cgcctctctc    3960
ccgggaagta tcttatcttg aaacctgatc tctaaatcat tcaaatattt attattgaag    4020
atttaccata agagactgga ccagaagtta ggagacctac taagatgcct aagccaaggt    4080
cctccggggc cgaattc                                                    4097
```

<210> SEQ ID NO 6
<211> LENGTH: 1205
<212> TYPE: PRT
<213> ORGANISM: Cytomegalovirus

<400> SEQUENCE: 6

Met Gly Asn Leu Lys Ser Val Gly Gln Glu Pro Gly Pro Pro Cys Gly
 1               5                  10                  15

Leu Gly Leu Gly Leu Gly Leu Gly Leu Cys Gly Lys Gln Gly Pro Ala
            20                  25                  30

Ser Pro Ala Pro Glu Pro Ser Arg Ala Pro Ala Pro Ala Thr Pro His

-continued

```
            35                  40                  45
Ala Pro Asp His Ser Pro Ala Pro Asn Ser Pro Thr Leu Thr Arg Pro
        50                  55                  60

Pro Glu Gly Pro Lys Phe Pro Arg Val Lys Asn Trp Glu Leu Gly Ser
 65                  70                  75                  80

Ile Thr Tyr Asp Thr Leu Cys Ala Gln Ser Gln Gln Asp Gly Pro Cys
                85                  90                  95

Thr Pro Arg Arg Cys Leu Gly Ser Leu Val Leu Pro Arg Lys Leu Gln
                100                 105                 110

Thr Arg Pro Ser Pro Gly Pro Pro Ala Glu Gln Leu Leu Ser Gln
            115                 120                 125

Ala Arg Asp Phe Ile Asn Gln Tyr Tyr Ser Ser Ile Lys Arg Ser Gly
            130                 135                 140

Ser Gln Ala His Glu Glu Arg Leu Gln Glu Val Glu Ala Glu Val Ala
145                 150                 155                 160

Ser Thr Gly Thr Ile His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
    210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
                260                 265                 270

Thr Glu Leu Cys Ile Gln His Gly Trp Thr Pro Gly Asn Gly Arg Phe
            275                 280                 285

Asp Val Leu Pro Leu Leu Leu Gln Ala Pro Asp Glu Ala Pro Glu Leu
        290                 295                 300

Phe Val Leu Pro Pro Glu Leu Val Leu Glu Val Pro Leu Gly Ala Pro
305                 310                 315                 320

His Thr Gly Val Val Arg Gly Pro Gly Leu Arg Trp Tyr Ala Leu Pro
                325                 330                 335

Ala Val Ser Asn Met Leu Leu Glu Ile Gly Gly Leu Glu Phe Ser Ala
                340                 345                 350

Ala Pro Phe Ser Gly Trp Tyr Met Ser Thr Glu Ile Gly Thr Arg Asn
            355                 360                 365

Leu Cys Asp Pro His Arg Tyr Asn Ile Leu Glu Asp Val Ala Val Cys
    370                 375                 380

Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
                405                 410                 415

Val Thr Ile Val Asp His His Ala Ala Thr Val Ser Phe Met Lys His
                420                 425                 430

Leu Asp Asn Glu Gln Lys Ala Arg Gly Gly Cys Pro Ala Asp Trp Ala
            435                 440                 445

Trp Ile Val Pro Pro Ile Tyr Gly Ser Leu Pro Pro Val Phe His Gln
        450                 455                 460
```

```
Glu Met Val Asn Tyr Ile Leu Ser Pro Ala Phe Arg Tyr Gln Pro Asp
465                 470                 475                 480

Pro Trp Lys Gly Ser Ala Thr Lys Gly Ala Gly Ile Thr Arg Lys Lys
                485                 490                 495

Thr Phe Lys Glu Val Ala Asn Ala Val Lys Ile Ser Ala Ser Leu Met
            500                 505                 510

Gly Thr Leu Met Ala Lys Arg Val Lys Ala Thr Ile Leu Tyr Ala Ser
        515                 520                 525

Glu Thr Gly Arg Ala Gln Ser Tyr Ala Gln Gln Leu Gly Arg Leu Phe
    530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Thr Ser Thr Phe
                565                 570                 575

Gly Asn Gly Asp Pro Pro Glu Asn Gly Glu Ser Phe Ala Ala Ala Leu
            580                 585                 590

Met Glu Met Ser Gly Pro Tyr Asn Ser Ser Pro Arg Pro Glu Gln His
        595                 600                 605

Lys Ser Tyr Lys Ile Arg Phe Asn Ser Val Ser Cys Ser Asp Pro Leu
    610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Val Phe Gly Leu Gly Ser
                645                 650                 655

Arg Ala Tyr Pro His Phe Cys Ala Phe Ala Arg Ala Val Asp Thr Arg
            660                 665                 670

Leu Glu Glu Leu Gly Gly Glu Arg Leu Leu Gln Leu Gly Gln Gly Asp
        675                 680                 685

Glu Leu Cys Gly Gln Glu Glu Ala Phe Arg Gly Trp Ala Lys Ala Ala
    690                 695                 700

Phe Gln Ala Ser Cys Glu Thr Phe Cys Val Gly Glu Glu Ala Lys Ala
705                 710                 715                 720

Ala Ala Gln Asp Ile Phe Ser Pro Lys Arg Ser Trp Lys Arg Gln Arg
                725                 730                 735

Tyr Arg Leu Ser Ala Gln Ala Glu Gly Leu Gln Leu Leu Pro Gly Leu
            740                 745                 750

Ile His Val His Arg Arg Lys Met Phe Gln Ala Thr Val Leu Ser Val
        755                 760                 765

Glu Asn Leu Gln Ser Ser Lys Ser Thr Arg Ala Thr Ile Leu Val Arg
    770                 775                 780

Leu Asp Thr Ala Gly Gln Glu Gly Leu Gln Tyr Gln Pro Gly Asp His
785                 790                 795                 800

Ile Gly Ile Ser Ala Pro Asn Arg Pro Gly Leu Val Glu Ala Leu Leu
                805                 810                 815

Ser Arg Val Glu Asp Pro Pro Pro Thr Glu Ser Val Ala Val Glu
            820                 825                 830

Gln Leu Glu Lys Gly Ser Pro Gly Gly Pro Pro Ser Trp Val Arg
        835                 840                 845

Asp Pro Arg Leu Pro Pro Cys Thr Val Arg Gln Ala Leu Thr Phe Phe
    850                 855                 860

Leu Asp Ile Thr Ser Pro Pro Ser Pro Arg Leu Leu Arg Leu Leu Ser
865                 870                 875                 880
```

```
                            -continued

Thr Leu Ala Glu Glu Pro Ser Glu Gln Glu Leu Glu Thr Leu Ser
            885                 890                 895

Gln Asp Pro Arg Arg Tyr Glu Glu Trp Lys Leu Val Arg Cys Pro Thr
            900                 905                 910

Leu Leu Glu Val Leu Glu Gln Phe Pro Ser Val Ala Leu Pro Ala Pro
        915                 920                 925

Leu Leu Leu Thr Gln Leu Pro Leu Leu Gln Pro Arg Tyr Tyr Ser Val
    930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
            965                 970                 975

Val Cys Ser Thr Trp Leu Ser Gln Leu Lys Thr Gly Asp Pro Val Pro
            980                 985                 990

Cys Phe Ile Arg Gly Ala Pro Ser Phe Arg Leu Pro Pro Asp Pro Tyr
        995                 1000                1005

Val Pro Cys Ile Leu Val Gly Pro Gly Thr Gly Ile Ala Pro Phe Arg
    1010                1015                1020

Gly Phe Trp Gln Glu Arg Leu His Asp Ile Glu Ser Lys Gly Leu Gln
1025                1030                1035                1040

Pro His Pro Met Thr Leu Val Phe Gly Cys Arg Cys Ser Gln Leu Asp
            1045                1050                1055

His Leu Tyr Arg Asp Glu Val Gln Asp Ala Gln Glu Arg Gly Val Phe
            1060                1065                1070

Gly Arg Val Leu Thr Ala Phe Ser Arg Glu Pro Asp Ser Pro Lys Thr
        1075                1080                1085

Tyr Val Gln Asp Ile Leu Arg Thr Glu Leu Ala Ala Glu Val His Arg
    1090                1095                1100

Val Leu Cys Leu Glu Arg Gly His Met Phe Val Cys Gly Asp Val Thr
1105                1110                1115                1120

Met Ala Thr Ser Val Leu Gln Thr Val Gln Arg Ile Leu Ala Thr Glu
            1125                1130                1135

Gly Asp Met Glu Leu Asp Glu Ala Gly Asp Val Ile Gly Val Leu Arg
            1140                1145                1150

Asp Gln Gln Arg Tyr His Glu Asp Ile Phe Gly Leu Thr Leu Arg Thr
        1155                1160                1165

Gln Glu Val Thr Ser Arg Ile Arg Thr Gln Ser Phe Ser Leu Gln Glu
    1170                1175                1180

Arg His Leu Arg Gly Ala Val Pro Trp Ala Phe Asp Pro Pro Gly Pro
1185                1190                1195                1200

Asp Thr Pro Gly Pro
            1205
```